US008658597B2

(12) United States Patent
Hansen et al.

(10) Patent No.: US 8,658,597 B2
(45) Date of Patent: Feb. 25, 2014

(54) STABILISED COMPOSITIONS OF FACTOR VII POLYPEPTIDES

(75) Inventors: Birthe Lykkegaard Hansen, Værløse (DK); Michael Bech Jensen, Allerød (DK); Troels Kornfelt, Virum (DK)

(73) Assignee: Novo Nordisk HealthCare AG, Zurich (CH)

( * ) Notice: Subject to any disclaimer, the term of this patent is extended or adjusted under 35 U.S.C. 154(b) by 225 days.

(21) Appl. No.: 12/407,266

(22) Filed: Mar. 19, 2009

(65) Prior Publication Data

US 2009/0181895 A1 Jul. 16, 2009

Related U.S. Application Data

(63) Continuation of application No. 11/450,783, filed on Jun. 9, 2006, now abandoned, which is a continuation of application No. PCT/EP2004/053587, filed on Dec. 17, 2004.

(60) Provisional application No. 60/531,728, filed on Dec. 22, 2003.

(30) Foreign Application Priority Data

Dec. 19, 2003 (DK) .................................. 2003 01901

(51) Int. Cl.
*A61K 38/14* (2006.01)
*A61K 38/36* (2006.01)
*A61P 7/04* (2006.01)

(52) U.S. Cl.
USPC ........ 514/13.7; 514/14.3; 514/14.4; 530/381; 530/384

(58) Field of Classification Search
USPC ............. 514/2, 12, 13.7, 14.3, 14.4; 530/350, 530/384, 381
See application file for complete search history.

(56) References Cited

U.S. PATENT DOCUMENTS

| | | | |
|---|---|---|---|
| 115,590 A | 6/1871 | Flood et al. | |
| 4,297,344 A | 10/1981 | Schwinn et al. | |
| 4,382,083 A | 5/1983 | Thomas | |
| 4,404,132 A | 9/1983 | Mitra | |
| 4,495,278 A | 1/1985 | Thomas | |
| 4,784,950 A | 11/1988 | Hagen et al. | |
| 4,956,386 A | 9/1990 | McLoughlin et al. | |
| 5,180,583 A | 1/1993 | Hedner | |
| 5,288,629 A | 2/1994 | Berkner | |
| 5,399,670 A | 3/1995 | Bhattacharya et al. | |
| 5,457,181 A | 10/1995 | Michalski et al. | |
| 5,576,291 A | 11/1996 | Curtis et al. | |
| 5,580,856 A | 12/1996 | Prestrelski et al. | |
| 5,649,959 A | 7/1997 | Hannam et al. | |
| 5,700,914 A | 12/1997 | Jørgensen et al. | |
| 5,750,358 A | 5/1998 | Morrissey | |
| 5,770,700 A | 6/1998 | Webb et al. | |
| 5,804,420 A | 9/1998 | Chan et al. | |
| 5,817,788 A | 10/1998 | Berkner et al. | |
| 5,824,780 A | 10/1998 | Curtis et al. | |
| 5,830,852 A | 11/1998 | Thatcher et al. | |
| 5,831,026 A | 11/1998 | Almstedt et al. | |
| 5,833,982 A | 11/1998 | Berkner et al. | |
| 5,874,408 A | 2/1999 | Nayar | |
| 5,925,738 A | 7/1999 | Miekka | |
| 5,925,739 A | 7/1999 | Spira et al. | |
| 5,962,650 A | 10/1999 | Osterberg et al. | |
| 5,993,795 A | 11/1999 | Osawa et al. | |
| 6,034,222 A | 3/2000 | Fischer et al. | |
| 6,183,743 B1 | 2/2001 | Hart et al. | |
| 6,228,620 B1 | 5/2001 | Chapman et al. | |
| 6,277,828 B1 | 8/2001 | Knepp et al. | |
| 6,310,183 B1 | 10/2001 | Johannessen et al. | |
| 6,320,029 B1 | 11/2001 | Miekka et al. | |
| 6,461,610 B1 | 10/2002 | Kongsbak et al. | |
| 6,586,573 B1 | 7/2003 | Besman et al. | |
| 6,586,574 B1 | 7/2003 | Hansen | |
| 6,599,724 B1 | 7/2003 | Mikaelsson et al. | |
| 6,750,053 B1 | 6/2004 | Widrig Opalsky et al. | |
| 6,806,063 B2 | 10/2004 | Pedersen et al. | |
| 6,825,323 B2 | 11/2004 | Hess | |
| 6,833,352 B2 | 12/2004 | Johannessen et al. | |
| 6,858,587 B2 | 2/2005 | Sorensen et al. | |
| 6,903,069 B2 | 6/2005 | Pingel et al. | |
| 6,908,610 B1 | 6/2005 | Sato | |
| 7,015,194 B2 | 3/2006 | Kjalke | |
| 7,078,479 B2 | 7/2006 | Rojkjaer | |
| 7,125,846 B2 | 10/2006 | Rojkjaer | |
| 7,173,000 B2 | 2/2007 | Ruf et al. | |

(Continued)

FOREIGN PATENT DOCUMENTS

| | | |
|---|---|---|
| AU | 2003/289742 | 7/2007 |
| CA | 2304396 | 4/1999 |

(Continued)

OTHER PUBLICATIONS

Enziklopedia lekarstv. M., RLS-2001, 468; Encyclopedia of drugs, p. 468.
International Search Report dated Oct. 20, 2003.
Wang et al., Journal of Parenteral Science & Technology, vol. 42, Supplement, pp. S3-S26 (1988).
Wells, Biochemistry, vol. 29, pp. 8509-8517 (1990).
Non-Final OA received by USPTO for U.S. Appl. No. 12/154,088 dated Jul. 29, 2009.
Notice of Allowance received by USPTO for U.S. Appl. No. 12/154,088 dated Feb. 1, 2010.
Non-Final Office Action mailed Nov. 12, 2010 in U.S. Appl. No. 11/526,503, filed Sep. 25, 2006 by Jensen et al.
Bach et al., 1984, "Immunoaffinity Purification of Bovine Factor VII," Blood 63(2):393-398.
Bajaj et al., 1981, "Isolation and Characterization of Human Factor VII," Journal of Biological Chemistry 256(1):253-259.
Blajchman, 2001, "Novel platelet products, substitutes and alternatives," Transfusion Clinique et Biologique 8(3):267-271.
Broze et al., 1980, "Purification and Properties of Human Coagulation Factor VII," Journal of Biological Chemistry 255(4):1242-1247.

(Continued)

*Primary Examiner* — Chih-Min Kam
(74) *Attorney, Agent, or Firm* — Jianjie Hu

(57) ABSTRACT

The invention relates to chemically as well as physically stable kits and compositions comprising polypeptides, in particular Factor VII or Factor VII-related polypeptides, such that these compositions can be stored, handled and used at room temperature.

17 Claims, No Drawings

(56) References Cited

U.S. PATENT DOCUMENTS

| | | | |
|---|---|---|---|
| 8,022,031 | B2 | 9/2011 | Hansen et al. |
| 8,026,214 | B2 | 9/2011 | Jensen et al. |
| 8,299,029 | B2 | 10/2012 | Jensen et al. |
| 8,318,904 | B2 | 11/2012 | Jensen et al. |
| 2001/0031721 | A1 | 10/2001 | Webb et al. |
| 2002/0110552 | A1 | 8/2002 | Romisch et al. |
| 2002/0115590 | A1 | 8/2002 | Johannessen et al. |
| 2003/0109446 | A1 | 6/2003 | Rojkjaer |
| 2004/0009918 | A1 | 1/2004 | Nedergaard et al. |
| 2004/0037893 | A1 | 2/2004 | Hansen et al. |
| 2004/0043933 | A1 | 3/2004 | Hansen et al. |
| 2004/0147439 | A1 | 7/2004 | Araki et al. |
| 2005/0266006 | A1 | 12/2005 | Rojkjaer |
| 2006/0009376 | A1 | 1/2006 | Eibl |
| 2006/0013812 | A1 | 1/2006 | Rojkjaer |
| 2006/0063714 | A1 | 3/2006 | Jensen et al. |
| 2006/0160720 | A1 | 7/2006 | Jensen et al. |
| 2006/0166882 | A1 | 7/2006 | Jensen et al. |
| 2007/0049523 | A1 | 3/2007 | Hansen et al. |
| 2008/0206225 | A1 | 8/2008 | Arentsen et al. |
| 2009/0075895 | A1* | 3/2009 | Nedergaard et al. ............ 514/12 |
| 2009/0181895 | A1* | 7/2009 | Hansen et al. .................. 514/12 |
| 2010/0136622 | A1 | 6/2010 | Krarup |
| 2010/0166730 | A1 | 7/2010 | Jensen et al. |

FOREIGN PATENT DOCUMENTS

| | | |
|---|---|---|
| CA | 2315309 | 2/2001 |
| CA | 2490342 | 12/2003 |
| DE | 19853033 | 5/2000 |
| EP | 0052874 | 6/1982 |
| EP | 225160 | 6/1987 |
| EP | 314095 A1 | 5/1989 |
| EP | 430200 | 6/1991 |
| EP | 547932 | 6/1993 |
| EP | 765669 | 7/1996 |
| EP | 770625 | 9/1996 |
| EP | 0872487 | 10/1998 |
| EP | 952215 | 10/1999 |
| EP | 1232753 | 8/2002 |
| JP | 62-195335 | 8/1987 |
| JP | 3-155797 | 7/1991 |
| JP | 6-504678 | 6/1994 |
| JP | 8-509745 | 10/1996 |
| JP | 11-500408 | 1/1999 |
| JP | 2000-302689 | 10/2000 |
| JP | 2000/513720 | 10/2000 |
| JP | 2001-515460 | 9/2001 |
| JP | 2003-507388 | 2/2003 |
| JP | 2003-531862 | 10/2003 |
| NZ | 336548 | 9/2001 |
| WO | WO 88/00210 | 1/1988 |
| WO | WO 91/10439 | 7/1991 |
| WO | WO 92/15686 | 9/1992 |
| WO | WO 93/00807 | 1/1993 |
| WO | WO 94/05692 | 3/1994 |
| WO | WO 94/22905 | 10/1994 |
| WO | WO 94/26286 | 11/1994 |
| WO | WO 94/27631 | 12/1994 |
| WO | WO 95/28954 | 11/1995 |
| WO | WO 96/12800 | 5/1996 |
| WO | WO 97/14430 | 4/1997 |
| WO | WO 97/19687 | 6/1997 |
| WO | WO 97/26909 | 7/1997 |
| WO | WO 97/47651 | 12/1997 |
| WO | WO 98/12225 | 3/1998 |
| WO | WO 98/22619 | 5/1998 |
| WO | WO 98/48822 | 11/1998 |
| WO | WO 99/02160 | 1/1999 |
| WO | WO 99/49880 | 10/1999 |
| WO | WO 99/66031 | 12/1999 |
| WO | WO 00/20835 | 4/2000 |
| WO | WO 00/48635 | 8/2000 |
| WO | WO 00/72873 | 12/2000 |
| WO | WO 01/03726 | 1/2001 |
| WO | WO 01/12653 | 2/2001 |
| WO | WO 01/17542 | 3/2001 |
| WO | WO 01/17567 | 3/2001 |
| WO | WO 01/17569 | 3/2001 |
| WO | WO 01/58935 | 8/2001 |
| WO | WO 01/82943 | 11/2001 |
| WO | WO 01/83725 | 11/2001 |
| WO | WO 01/85198 | 11/2001 |
| WO | WO 01/85199 | 11/2001 |
| WO | WO 02/17957 | 3/2002 |
| WO | WO 02/22776 | 3/2002 |
| WO | WO 03/002524 | 1/2003 |
| WO | WO 03/006054 | 1/2003 |
| WO | WO 03/007868 | 1/2003 |
| WO | WO 03/055511 | 7/2003 |
| WO | WO 03/055512 | 7/2003 |
| WO | WO 03/092731 | 11/2003 |
| WO | WO 2004/000347 | 12/2003 |
| WO | WO 2004/008635 | 1/2004 |
| WO | WO 2004/082708 | 9/2004 |
| WO | WO 2004/110469 | 12/2004 |
| WO | 2005/058283 | 6/2005 |
| WO | 2006/114448 A2 | 11/2006 |

OTHER PUBLICATIONS

Brozovic et al., 1971, "Stability of Prothrombin and Factor VII in Freeze-Dried Plasma," Journal of Clinical Pathology 24:690-693.

Dike et al., 1980, "A Factor VII Concentrate for Therapeutic Use," British Journal of Haematology 45:107-118.

Dombrose et al., 1973, "Evidence for Multiple Molecular Forms of Autoprothrombin C (Factor XA)," Thrombosis Research 3:737-743.

Husi et al., 1999, "Separation of Human Vitamin K-Dependent Coagulation Proteins Using Hydrophobic Interaction Chromatography," Journal of Chromatography B 736:77-88.

Jesty et al., 1974, "Purification of Factor VII From Bovine Plasma," Journal of Biological Chemistry 249(2):509-515.

Klausen, N.K et al., 1995, "Analysis of the Glycoforms of Human Recombinant Factor VIIA by Capillary Electrophoresis and High-Performance Liquid Chromatography" Journal of Chromatography A 718:195-202.

Krarup et al., 2003, "Studies on Coagulation Factor VIIA . . . " Abstracts of Papers—American Chemical Society 225(1-2):201-202, Abstract#: BIOT333.

English Translation of Krylov, Chief Editor, 2001, Enziklopedia Lekarstv. M., (Encyclopaedia of Medicines/Drugs) RLS-2001, 468; Encyclopedia of Drugs, pp. 468.

Liebman et al., 1985, "Immunoaffinity Purification of Factor IX (Christmas Factor) by Using Conformation-Specific Antibodies Directed Against the Factor IX-Metal Complex," Proceedings of the National Academy of Sciences of the USA 82:3879-3883.

Nemerson et al., 1973, "Activation of a Proteolytic System by a Membrane Lipoprotein: Mechanism of Action of Tissue Factor," Proceedings of the National Academy of Sciences of the USA 70(2):310-314.

Novo Nordisk, 2000, "Koagulationsfaktor VIIA," Lægemiddel Kataloget pp. 893-894 and English Translation.

Novo Nordisk, 1999, "Novoseven Coagulation Factor VIIA (Recombinant)," FDA Article Online pp. 1-24.

O'Brien et al., 1991, "Purification and Characterization of Factor VII 304-GLN: A Variant Molecule With Reduced Activity Isolated From a Clinically Unaffected Male," Blood 78(1):132-140.

PCT/DK2004/000183 International Search Report, dated Jul. 22, 2004.

PCT/DK2004/000359 International Search Report dated Oct. 1, 2004.

Rao et al., 1984, "Purification of Human Factor VII Utilizing O-(Diethylaminoethyl)-Sephadex and Sulfopropyl-Sephadex Chromatography," Analytical Biochemistry 136(2):357-361.

Ruiz et al., 2000, "Expression and Purification of Recombinant Rabbit Factor VII," Thrombosis Research 98:203-211.

Sichler et al., 2002, "Crystal Structures of Uninhibited Factor VIIa Link its Cofactor and Substrate-Assisted Activation to Specific Interactions," J. Molecular Biology 322(3):591-603.

(56) References Cited

OTHER PUBLICATIONS

Tomokiyo et al., 2003, "Large-Scale Production and Properties of Human Plasma-Derived Activated Factor VII Concentrate" VOX Sanguinis 84:54-64.
Wang et al., 1988, "Parenteral Drug Association Objectives," Journal of Parenteral Science & Technology 42:2S.
Yan, 1996, "Review of Conformation-Specific Affinity Purification Methods for Plasma Vitamin K-Dependent Proteins," Journal of Molecular Recognition 9:211-218.
DE 19853033 English Abstract May 25, 2000.
JP 2000-302689 Machine Translation, Oct. 31, 2000.
JP 11-500408 English Language Machine Translation, published Jan. 12, 1999 (ZymoGenetics and Novo Nordisk A/S).
JP 8-509745 English Language Machine Translation, published Oct. 15, 1996.
JP 6-504678 English Abstract, Mar. 9, 2010.
JP 62-195335 English Abstract, Mar. 9, 2010.
Non-Final Office Action mailed Jun. 8, 2010 in U.S. Appl. No. 12/617,471, filed Nov. 12, 2009 by Jensen et al.
Non-Final Office Action mailed Jul. 2, 2010 in U.S. Appl. No. 12/536,872, filed Aug. 6, 2009 by Jensen et al.
Notice of Allowance mailed Jul. 30, 2010 in U.S. Appl. No. 12/154,088, filed May 20, 2008 by Hansen et al.
Notice of Allowance mailed Apr. 14, 2010 in U.S. Appl. No. 12/154,088, filed May 20, 2008 by Hansen et al.
Final Office Action mailed Aug. 26, 2010 in U.S. Appl. No. 11/526,503, filed Sep. 25, 2006 by Jensen et al.
Non-Final Office Action mailed Jan. 4, 2010 in U.S. Appl. No. 11/526,503, filed Sep. 25, 2006 by Jensen et al.
Non-Final Office Action mailed Apr. 6, 2009 in U.S. Appl. No. 11/526,503, filed Sep. 25, 2006 by Jensen et al.
Notice of Abandonment mailed Jul. 14, 2010 in U.S. Appl. No. 11/473,387, filed Jun. 21, 2006 by Hansen et al.
Final Office Action mailed Dec. 30, 2009 in U.S. Appl. No. 11/473,387 filed Jun. 21, 2006 by Hansen et al.
Non-Final Office Action mailed Jan. 29, 2009 in U.S. Appl. No. 11/473,387, filed Jun. 21, 2006 by Hansen et al.
Non-Final Office Action mailed Apr. 8, 2008 in U.S. Appl. No. 11/473,387, filed Jun. 21, 2006 by Hansen et al.
Notice of Abandonment mailed Apr. 7, 2009 in U.S. Appl. No. 11/450,783, filed Jun. 9, 2006 by Hansen et al.
Non-Final Office Action mailed Sep. 19, 2008 in U.S. Appl. No. 11/450,783, filed Jun. 9, 2006 by Hansen et al.
Notice of Allowance mailed Aug. 11, 2009 in U.S. Appl. No. 11/353,335, filed Feb. 14, 2006 by Jensen et al.
Non-Final Office Action mailed Jan. 13, 2009 in U.S. Appl. No. 11/353,335, filed Feb. 14, 2006 by Jensen et al.
Non-Final Office Action mailed Jul. 11, 2008 in U.S. Appl. No. 11/353,335, filed Feb. 14, 2006 by Jensen et al.
Notice of Abandonment mailed Jun. 10, 2008 in U.S. Appl. No. 11/304,429, filed Dec. 15, 2005 by Hansen et al.
Non-Final Office Action mailed Nov. 20, 2007 in U.S. Appl. No. 11/304,429, filed Dec. 15, 2005 by Hansen et al.
Non-Final Office Action mailed Apr. 18, 2007 in U.S. Appl. No. 11/304,429, filed Dec. 15, 2005 by Hansen et al.
Notice of Allowance mailed Apr. 8, 2010 in U.S. Appl. No. 11/304,427, filed Dec. 15, 2005 by Jensen et al.
Notice of Allowance mailed Dec. 15, 2009 in U.S. Appl. No. 11/304,427, filed Dec. 15, 2005 by Jensen et al.
Non-Final Office Action mailed Feb. 6, 2009 in U.S. Appl. No. 11/304,427, filed Dec. 15, 2005 by Jensen et al.
Advisory Action mailed Oct. 23, 2008 in U.S. Appl. No. 11/304,427, filed Dec. 15, 2005 by Jensen et al.
Final Office Action mailed May 2, 2008 in U.S. Appl. No. 11/304,427, filed Dec. 15, 2005 by Jensen et al.
Non-Final Office Action mailed Sep. 11, 2007 in U.S. Appl. No. 11/304,427, filed Dec. 15, 2005 by Jensen et al.
Notice of Abandonment mailed Apr. 17, 2007 in U.S. Appl. No. 11/304,427, filed Dec. 15, 2005 by Jensen et al. and Decision of Petition to Reinstate Granted.
Non-Final Office Action mailed Aug. 27, 2010 in U.S. Appl. No. 11/284,709, filed Nov. 22, 2005 by Jensen et al.
Final Office Action mailed Feb. 19, 2010 in U.S. Appl. No. 11/284,709, filed Nov. 22, 2005 by Jensen et al.
Non-Final Office Action mailed Jun. 4, 2009 in U.S. Appl. No. 11/284,709, filed Nov. 22, 2005 by Jensen et al.
Non-Final Office Action mailed Sep. 25, 2008 in U.S. Appl. No. 11/284,709, filed Nov. 22, 2005 by Jensen et al.
Non-Final Office Action mailed Aug. 6, 2007 in U.S. Appl. No. 11/284,709, filed Nov. 22, 2005 by Jensen et al.
Notice of Allowance mailed May 6, 2010 in U.S. Appl. No. 11/229,428, filed Sep. 15, 2005 by Krarup et al.
Notice of Allowance mailed Jan. 12, 2010 in U.S. Appl. No. 11/229,428, filed Sep. 15, 2005 by Krarup et al.
Notice of Allowance mailed Aug. 28, 2009 in U.S. Appl. No. 11/229,428, filed Sep. 15, 2005 by Krarup et al.
Notice of Allowance mailed May 28, 2009 in U.S. Appl. No. 11/229,428, filed Sep. 15, 2005 by Krarup et al.
Non-Final Office Action mailed Oct. 1, 2008 in U.S. Appl. No. 11/229,428, filed Sep. 15, 2005 by Krarup et al.
Notice of Abandonment mailed Nov. 9, 2009 in U.S. Appl. No. 11/229,427, filed Sep. 15, 2005 by Jensen et al.
Notice of Allowance mailed Jun. 12, 2009 in U.S. Appl. No. 11/229,427, filed Sep. 15, 2005 by Jensen et al.
Advisory Action mailed Apr. 8, 2009 in U.S. Appl. No. 11/229,427, filed Sep. 15, 2005 by Jensen et al.
Final Office Action mailed Jan. 27, 2009 in U.S. Appl. No. 11/229,427, filed Sep. 15, 2005 by Jensen et al.
Non-Final Office Action mailed Jun. 25, 2008 in U.S. Appl. No. 11/229,427, filed Sep. 15, 2005 by Jensen et al.
Non-Final Office Action mailed Nov. 21, 2007 in U.S. Appl. No. 11/229,427, filed Sep. 15, 2005 by Jensen et al.
Notice of Abandonment mailed Oct. 27, 2006 in U.S. Appl. No. 10/609,780, filed Jun. 30, 2003 by Jensen et al.
Non-Final Office Action mailed Mar. 27, 2006 in U.S. Appl. No. 10/609,780, filed Jun. 30, 2003 by Jensen et al.
Notice of Allowance mailed Jun. 22, 2010 in U.S. Appl. No. 10/602,838, filed Jun. 24, 2003 by Hansen et al.
Notice of Allowance mailed Mar. 29, 2010 in U.S. Appl. No. 10/602,838, filed Jun. 24, 2003 by Hansen et al.
Notice of Allowance mailed Dec. 8, 2009 in U.S. Appl. No. 10/602,838, filed Jun. 24, 2003 by Hansen et al.
Final Office Action mailed Jul. 31, 2009 in U.S. Appl. No. 10/602,838, filed Jun. 24, 2003 by Hansen et al.
Non-Final Office Action mailed Feb. 6, 2009 in U.S. Appl. No. 10/602,838, filed Jun. 24, 2003 by Hansen et al.
Advisory Action mailed Sep. 3, 2008 in U.S. Appl. No. 10/602,838, filed Jun. 24, 2003 by Hansen et al.
Final Office Action mailed Feb. 7, 2008 in U.S. Appl. No. 10/602,838, filed Jun. 24, 2003 by Hansen et al.
Non-Final Office Action mailed May 31, 2007 in U.S. Appl. No. 10/602,838, filed Jun. 24, 2003 by Hansen et al.
Advisory Action mailed Mar. 14, 2007 in U.S. Appl. No. 10/602,838, filed Jun. 24, 2003 by Hansen et al.
Final Office Action mailed Oct. 12, 2006 in U.S. Appl. No. 10/602,838, filed Jun. 24, 2003 by Hansen et al.
Non-final Office Action mailed Feb. 7, 2006 in U.S. Appl. No. 10/602,838, filed Jun. 24, 2003 by Hansen et al.
Notice of Abandonment mailed Aug. 2, 2006 in U.S. Appl. No. 10/602,340, filed Jun. 23, 2003 by Hansen et al.
Notice of Abandonment mailed Jan. 5, 2009 in U.S. Appl. No. 10/427,395, filed May 1, 2003 by Nedergaard et al.
Non-Final Office Action mailed May 30, 2008 in U.S. Appl. No. 10/427,395, filed May 1, 2003 by Nedergaard et al.
Advisory Action mailed Aug. 3, 2007 in U.S. Appl. No. 10/427,395, filed May 1, 2003 by Nedergaard et al.
Final Office Action mailed Mar. 19, 2007 in U.S. Appl. No. 10/427,395, filed May 1, 2003 by Nedergaard et al.
Non-Final Office Action mailed Jun. 14, 2006 in U.S. Appl. No. 10/427,395, filed May 1, 2003 by Nedergaard et al.
Tubek et al., "Role of Zinc in Hemostasis: A Review," Biol Trace Elem Res, 2008, vol. 121, pp. 1-8.

(56) References Cited

OTHER PUBLICATIONS

Laegemiddel Kataloget (The Medicine Catalogue), pp. 893-894 (2000) and English translation.
English language machine translation for JP11500408, published Jan. 12, 1999 (ZymoGenetics and Novo Nordisk A/S).
English language abstract for JP6504678, published Jun. 2, 1994 (ZymoGenetics and Novo Nordisk A/S).
English language abstract for JP62195335, published Aug. 28, 1987 (Novo Industri A/S).
*Whirlpool Co. v. Camco On.* 2 S.C.R. 1067 2000.
*GlaxoSmithKline Inc. v. Apotex Inc.* F.C.T 687 2003.
English language abstract for JP8509745, published Oct. 15, 1996 (Pharmacia & Upjohn).
EP 765669 English Abstract Apr. 2, 1997.
JP 3-155797 English Abstract, Mar. 7, 1991.
JP 2000-513720 English Language Machine Translation, published Oct. 17, 2000 (Novo Nordisk A/S).
Manning, M.C et al. Pharmaceutical Research Stability of Protein Pharmaceuticals 1989 6 11 903-918.
Head et al., 1997, Thrombosis Research, vol. 85, No. 4, pp. 327-329.
Definition of analog from http://cancerweb.ncl.ac.uk/omd/about. html, pp. 1-5. Accessed Jul. 7, 2005.
Factor VII sequence from MCBI, AAA51983, pp. 1-2. Accessed May 17, 2012.
Rudinger J, "Characteristics of the amino acids as components of a peptide hormone sequence", Peptide Hormones, JA Parsons Edition, University Park Press, Jun. 1976, pp. 1-7.
"Designing Custom Peptides", from SIGMA Genosys, pp. 1-2. Acessed Dec. 16, 2004.
Schinzel R, Drueckes P, "The Phosphate recognition site of *Escherichia coli* maltodextrin phosphorylase", FEBS, Jul. 1991, 286 (1,2): 125-128.
Berendsen HJC, "A Glimpse of the Holy Grail?" Science, 1998, 282:642-643.
Voet D, Voet JG, Biochemistry. Second Edition, John Wiley & Sons, Inc., 1995, pp. 235-241.
Ngo JT, Marks J, Karplus M, "Comoutational Complexity, Protein Structure Prediction, and the Levinthal Paradox", The Protein Folding Problem and Tertiary Structure Prediction, K. Merc Jr. and S. Le Garnd Edition, 1994, pp. 491-495.
Bradley CM, Barrick D, "Limits of Copperativity in a Structurally Modular Protein: Response of the Notch Ankyrin Domain to Analogous Alanine Substitutions in Each Repeat", J. Mol. Biol., 2002, 324:373-386.
Moscardo, F. et al., British Journal of Haematology, "Successful Treatment of Severe Intra-Abdominal Bleeding Associated With Disseminated Intravascular Coagulation Using Recombinant Activated Factor VII", 2001, vol. 113, pp. 174-176.
Shapiro et al., Thrombosis and Haemostasis, "Prospective, Randomised Trial of Two Doses of rFVIIa (NovoSeven) in Haemophilia Patients With Inhibitors Undergoing Surgery", 1998, vol. 80, pp. 773-778.
Marmur, J., Thrombosis, Hemostasis, and Blood Clotting, Downloaded Dec. 13, 2010.
Horioka et al, Injection-Its Basics, Preparation and Application, 1st Edition, Mar. 22, 1995, Publiushed by Nanzandou, p. 19-23.
Iyakuhin Tenkabutsu Jiten(Pharmaceutical Excipients Dictionary) 2000, Edited by International Pharmaceutical Excipients Council Japan, 1st Edition, Apr. 28, 2000, Published by Yakuji Nippo Ltd, p. 281.
Ammonium Sulfate Precipitation, http://en.wikipedia.org/w/index. php? title=ammonium_sulfate_precipitation&oldid=440160162, From Wikipedia, the free encyclopedia, 2012.
Hofmeister Series,http://en.wikipedia.org/w/index.php? title=hofmeister_series&oldid=502630992, From Wikipedia, Üie fres encyclopedia, 2012.
Wang, Yu-Chang John et al, Parenteral Formulations of Proteins and Peptides: Stability and Stabilizers, J Parenter Sci Technol, 1988, vol. 42, pp. S2-S26.
Cleland, J.L. et al., Crit Rev in Thera Drug Can Sys., vol. 10 (4), pp. 307-377 (1993).
Wang, Y-C.J. et al., J Parenter Sci Technol., vol. 42 (10), pp. 4-26 (1988).
Manning et al., Pharm Res., vol. 6, (11), pp. 903-918 (1989).
Wang, International Journal of Pharmaceutics, vol. 203, pp. 1-60 (2000).
International Search Report of PCT/DK03/00419, (2003).
International Search Report of PCT/DK2004/000181, (2005).
Porter, C.W. et al., Biochem & Biophys Res Comm., vol. 122(1), pp. 350-357 (1984).
Cooper, Arthur J.L., Ann Rev Biochem, vol. 52, pp. 187-222 (1983).
NovoSeven® Coagulation Factor VIIa (Recombinant) Package Insert, (issued on 2005).
Akers et al., Peptides and Proteins as Parenteral Solutions, Pharmaceutical Formulation Development of Peptides and Proteins, 2000, pp. 145-158.
Bedu-Addo et al., Preformulation Development of Recombinant Pegylated Staphylokinase SY161 Using Statistical Design, AAPS PharmSci, 2002, vol. 4, No. 4, pp. 1-13.
Chen et al., Stabilization of Recombinant Human Keratinocyte Growth Factor by Osmolytes and Salts, Journal of Phanvaceutical Sciences, 1996, vol. 85, No. 4, pp. 419-422.

\* cited by examiner

STABILISED COMPOSITIONS OF FACTOR VII POLYPEPTIDES

CROSS-REFERENCE TO RELATED APPLICATIONS

This application is a continuation of U.S. patent application Ser. No. 11/450,783, filed Jun. 9, 2006, which is a continuation of International Patent Application No. PCT/EP2004/053587, filed Dec. 17, 2004, which claims priority from Danish Patent Application No. PA 2003 01901, filed Dec. 19, 2003; and to U.S. Patent Application No. 60/531,728, filed Dec. 22, 2003.

FIELD OF INVENTION

The present invention relates to kits comprising chemically as well as physically stable compositions comprising Factor VII or a Factor VII-related polypeptide such that these compositions can be stored, handled and used at room temperature.

BACKGROUND OF THE INVENTION

Medicaments containing polypeptides are complex compositions. When developing such a medicament several parameters need to be considered. By example, the medicament needs to be effective, safe and lead to good patient compliance. Moreover, the medicament may be formulated for parenteral administration using pharmaceutically acceptable excipients, which will have to meet with the approval of various world-wide medical regulatory agencies. For the purpose of parenteral administration, it is highly desirable that the formulation is approximately isotonic and that the pH of the formulation is in a physiologically suitable range upon injection/infusion, otherwise it may result in pain and discomfort for the patient. For a general review of polypeptide formulations, see, for example, Cleland et al.: The development of stable protein formulations: A closer look at protein aggregation, deamidation and oxidation, Critical Reviews in Therapeutic Drug Carrier Systems 1993, 10(4): 307-377; and Wang et al., Parenteral formulations of polypeptides and peptides: Stability and stabilizers, Journal of Parenteral Science and Technology 1988 (Supplement), 42 (2S).

However, for medicaments comprising polypeptides the safety may directly be related to the physical and chemical stability of the polypeptide. Polypeptides are susceptible to physical degradation, including denaturation and aggregation such as the formation of soluble or insoluble aggregates in the form of dimers, oligomers and polymers, or to chemical degradation, including for example, hydrolysis, deamidation and oxidation. Consequently, the said physical and chemical instability may lead to loss of activity of the polypeptide, formation of toxic and immunogenic degradation products, in case of coagulation factor polypeptides there is serious risk of introducing thrombosis upon injection of the degraded polypeptides, clogging of needles used for injections and risk of non-homogeneity, to name just a few.

Thus, compositions comprising polypeptides need to be stabilised so as allowing storage and handling at ambient temperatures. One approach of stabilising a polypeptide relates to removal of water from the polypeptide, e.g. such as providing the polypeptide in the form of a lyophilised cake, the final matter obtained in a freeze-drying process. However, the freeze-drying process itself is also harmful to polypeptides; during freeze-drying, the polypeptide solution is first cooled until adequately frozen and bulk water in the polypeptide solution will form ice at this stage. The polypeptide is hereby prone to freeze-induced stress resulting in deformation and precipitation. In the next step, the so-called primary drying stage, the ice sublimes and in the secondary drying stage, adsorbed or bound water is removed under elevated temperatures. During this water removal, the polypeptides may loose their proper conformation that is provided mainly through hydrogen bonding.

Therefore, to preserve polypeptide conformation, activity and stability during freeze-drying, the polypeptide solution needs to be supplemented with sufficient amounts of proper excipients with cryoprotectant and/or lyoprotectant properties so as to protect the polypeptide from freeze-induced stress and/or stress during removal of water, respectively.

U.S. 20010031721 A1 (American Home Products) concerns highly concentrated, lyophilised, and liquid Factor IX formulations.

WO 97/26909 (Genetics Institute) concerns lyophilised preparations of Factor IX suitable for storage and administration. The preparations may comprise sucrose or mannitol as a cryoprotectant.

WO 95/28954 (Genetics Institute) concerns preparations of Factor IX suitable for storage and administration. The preparations may comprise sucrose as a cryoprotectant.

Additionally, when providing a lyophilised product, an essential feature relates to the properties of the lyophilised cake. It needs to have good properties as to its form and structure, i.e. it should not collapse in that such collapsed cakes can be hard or even impossible to dissolve (reconstitute) before use. Conversely, the physical structure of the lyophilised cake may not be too loosen and soft. Therefore, one or more so-called bulking agents are added to the polypeptide solution before freeze-drying.

Apart from choosing the right bulking agents it is also essential to avoid excipients which destabilises the physical properties of the cake. The concentration of these substances should be as low as possible. Furthermore, it is important that the reconstituted solution is not too hypotonic or hypertonic as this will cause injection inconvenience or even pain for the patient when administered. Therefore, it is normally necessary to add tonicity to the composition. Another excipient could be a buffer substance in order to keep the pH of the reconstituted solution stable during storage.

Vitamin K-dependent polypeptides are a group of polypeptides involved in the blood clotting process; the group include factor VII, factor IX, factor X, factor II, Protein C, Protein S, gas6, and bone matrix Gla polypeptide or can be a protease selected from the group consisting of factor VIIa, factor IXa, factor Xa, factor IIa, and activated protein C. Factors VIIa, IXa, and Xa are particularly useful proteases. Factor VIII is a polypeptides involved in the blood clotting process. It can be made by recombinant techniques or prepared from plasma and is widely used in treatment of bleeding episodes in haemophilia patients.

Factor VII is a polypeptide involved in the blood clotting process. Today, Factor VIIa can be made by recombinant techniques (rFVIIa) and is widely used as a pro-haemostatic agent. Factor VII (human wild-type) has been described in U.S. Pat. No. 4,784,950. rFVIIa offers today a rapid and highly effective pro-haemostatic response in haemophilic individuals experiencing bleeding. Advantageously, rFVIIa can be used for treating haemophilic individuals that cannot be treated with other coagulation factor products due to antibody formation. Also individuals suffering from Factor VII deficiency or individuals having a normal coagulation system but still experiencing excessive bleeding can be treated successfully with rFVIIa.

Today, recombinantly-made FVII polypeptide is provided as freeze-dried product that is meant to be stored at temperatures between about 2 and about 8° C. The requirement of cooled conditions causes a burden to and is inconvenient for the manufacturer or provider as well as the end user (the patient).

The actual recombinantly-made FVII product is NovoSeven® (Novo Nordisk A/S, Denmark) that consists of 1.2 mg recombinant human Factor VIIa, 5.84 mg NaCl, 2.94 mg CaCl2, 2H2O, 2.64 mg Glycylglycine, 0.14 mg polysorbate 80 and 60.0 mg mannitol. When reconstituted by 2.0 ml of water for injection (WFI), the pH is 5.5 and the thus prepared FVII-containing solution is sufficiently stable for 24 hours at room temperature.

The present investigators have found that upon storage of the lyophilised NovoSeven® product for 6 months at 25° C. about 6 to 7% w/w of the initial content of the rFVIIa is present in the form of aggregates.

Thus, compositions comprising Factor VII polypeptides need to be stabilised so as allowing storage and handling at ambient temperatures.

It is an objective of the present invention to provide improved compositions, kits, and methods for producing these, wherein the dry compositions comprising the polypeptides are stabilized against chemical and physical degradation (such as, e.g., forming less dimer/oligomer degradation forms); with good properties of the lyophilised cake as to its form and structure, i.e. it should not collapse; with good and stable physical structure of the lyophilised cake; where the dry composition is devoid of excipients which destabilises the physical properties of the cake, e.g., by decreasing the eutectic melting point and thus increasing the risk of collapse of the cake; wherein the reconstituted composition prepared by dissolving the dry polypeptide-containing composition in the administration vehicle is isotonic, or closely isotonic, and has a well-defined pH (pH-stable). Particularly, it is an object to provide improved compositions comprising Factor VII polypeptides, substantially without the presence of degradation products and without decreased activity of the Factor VII polypeptides, preferable after prolonged storage at ambient conditions, e.g. for at least 6 months. Furthermore, it is an objective that the stable compositions are suitable for parenteral administration so as not to cause any inconvenience for the patient.

SUMMARY OF THE INVENTION

It has been found by the present investigators that polypeptide-containing medicaments can be provided as a kit of parts comprising a first unit form consisting of a dry (e.g., a freeze-dried) composition comprising a polypeptide and at least one stabilizing agent wherein the composition has a moisture content of not more than about 3%, and container means for containing said first unit form; and, in container means for containing such a unit, a second unit form consisting of an administration vehicle comprising a solvent for solution (reconstitution) of said composition and at least one of the components selected from the list of: (i) an agent suitable for keeping the pH of said composition in the range of 3 to 9 when dissolved in aqueous solvent in an amount of from about 0.1 mM to 100 mM; and (ii) a tonicity modifying agent in an amount sufficient to make essentially isotonic the reconstituted solution resulting from dissolving the composition of the first unit form in the administration vehicle of the second unit form.

Substances which usually are present in the formulation like buffer substances and tonicity modifiers will very often decrease the eutectic melting point and will increase the risk of collapse of the cake. If these substances are present during freeze drying the temperature of the ice during the primary drying must be lowered to avoid collapse and consequently the time for freeze drying is prolonged. The concentration of these substances in the freeze-dried cake should be as low as possible or they should be completely avoided. Instead they may beneficially be added to the reconstitution liquid.

By lowering the concentration of these excipients or completely removing them, the reconstituted solution will in some instances become hypotonic and it is necessary the add tonicity modifiers to the solvent so as to obtain a solution with the needed tonicity, such as isotonicity, or closely so ("essentially isotonic"). Another necessary excipient in the solvent could be a buffer substance in order to keep the pH of the reconstituted solution stable during storage.

The kit of parts is sufficiently stable so as to allow for storage at room temperature for about at least 8 months.

Furthermore, it has been found that Factor VII polypeptides can be provided in a composition that is sufficient stable so as to allow for storage at room temperature for about at least 8 months. The investigators have found that the stabilisation relates to the proper combining of some pharmaceutically acceptable excipients.

Accordingly, the present invention relates in a first aspect to a kit (containing a pharmaceutical medicament/treatment), said kit comprising a) a composition comprising a polypeptide and at least one stabilizing agent, wherein the composition has a moisture content of not more than about 3%, in a first unit form, and container means for containing said first unit form; and b) an administration vehicle comprising a solvent for reconstitution (solution) of said composition and at least one of the components selected from the list of:
  (i) an agent suitable for keeping the pH of said composition in the range of 3 to 9 when dissolved in aqueous solvent, wherein the agent is present in an amount of from about 0.1 mM to 100 mM,
  (ii) a tonicity modifying agent in an amount sufficient to make the reconstituted solution resulting from dissolving the composition of the first unit form in the administration vehicle of the second unit form essentially isotonic;

in a second unit form, and container means for containing said second unit form.

In a second aspect, the invention relates to a method for preparing a liquid formulation of a polypeptide, the method comprising the steps of:

a) providing a first and a second unit form as described above, and b) mixing said first and second unit forms so as to provide a dissolved liquid solution of the composition in the administration vehicle.

In a third and fourth aspect, the invention relates to a method for treating a coagulation factor-responsive syndrome, comprising administering to a subject in need thereof an effective amount of a liquid formulation of a coagulation factor prepared by the method described above, and to the use of said formulation for the preparation of a medicament in the form of a kit as defined above for treatment of a Factor VII-responsive syndrome.

In a fifth aspect, the invention relates to a composition comprising a Factor VII polypeptide, and at least one stabilizing agent selected from the group consisting of a) a combination of an antioxidant and mannitol;

b) a combination of methionine and a polyol;

c) a combination of a saccharide and mannitol;
d) a combination of sucrose and a polyol;
e) methionine; and
a polysorbate surfactant in an amount of from about 0.06 to 0.08 mg/mL;
said composition having a moisture content of not more than about 3%;

In a sixth aspect, the invention relates to a method of preparing the above defined compositions, comprising the steps of:
i) providing a Factor VII polypeptide in a solution comprising at least one stabilizing agent selected from the group consisting of
a) a combination of an antioxidant and mannitol;
b) a combination of methionine and a polyol;
c) a combination of a saccharide and mannitol;
d) a combination of sucrose and a polyol; and
e) methionine; and
a polysorbate surfactant in an amount of from about 0.06 to 0.08 mg/mL;
ii) processing said solution so as to obtain a solid composition with a moisture content not more than about 3% w/w.

In a seventh and eighth aspect, the invention relates to a method for treating a FVII-responsive syndrome, comprising administering to a subject in need thereof an effective amount of a composition as defined above, and to the use of Factor VII polypeptide for the preparation of a medicament for treating a Factor VII-responsive syndrome, said medicament comprising a composition as defined above.

DETAILED DESCRIPTION OF THE INVENTION

The present invention relates to storage-stable kits and compositions comprising polypeptides, including FVIII polypeptides, Vitamin K-dependent polypeptides, and FVII polypeptides. The compositions can be stored at room temperature for an extended period of time without causing substantial degradation of the polypeptide. By room temperature is meant the ambient temperature inside a room; it normally ranges from about 5° C. to about 40° C., such as from about 10° C. to 30° C., or 15° C. to 25° C.

By proper predetermined combination of particular pharmaceutically acceptable excipients, the present investigators have provided stabilised compositions comprising polypeptides, particularly Factor VII polypeptides, thus allowing the compositions to be stored at room temperature for an extended period of time such as at least about 8 months. Advantageously, the stabilised compositions need not to be stored at cooled conditions, such as between 2 and 8° C.

The present invention also concerns storage-stable compositions that are stable for at least about 8 months upon storage at about 30° C. The composition is preferably stored in the dark. Thus, the present invention makes it possible to store such compositions at room temperature without increasing the risk of adverse events to the patient administering such compositions. Advantageously, the improved storage-stability will also result in reduced cost in that no special cooled conditions are required upon storage, further resulting in more convenient handling of the composition by the user.

Polypeptides to be formulated in accordance with the present invention includes, without limitation, blood coagulation factors including vitamin K-dependent polypeptides, such as, e.g., without limitation, factor VIII, factor V, factor XI, factor VII, factor IX, factor X, factor II, Protein C, Protein S, gas6, and bone matrix Gla polypeptide; activated FVIII, factor Va, factor XIa, factor VIIa, factor IXa, factor Xa, factor IIa, and activated Protein C.

The term "Vitamin K-dependent polypeptide" includes polypeptides selected from the group consisting of factor VII, factor IX, factor X, factor II, Protein C, Protein S, gas6, and bone matrix Gla polypeptide or can be a protease selected from the group consisting of factor VIIa, factor IXa, factor Xa, factor IIa, and activated Protein C. Factors VIIa, IXa, and Xa are particularly useful proteases.

The term "Factor VII polypeptide" is denoted to mean any Factor VII polypeptide that is effective in preventing or treating bleeding. This includes Factor VII polypeptides derived from blood or plasma, or produced by recombinant means.

As used herein, "Factor VII polypeptide" encompasses, without limitation, Factor VII, including variants thereof, as well as Factor VII-related polypeptides, Factor VII derivatives and Factor VII conjugates. The term "Factor VII" is intended to encompass, without limitation, polypeptides having the amino acid sequence 1-406 of wild-type human Factor VII (as disclosed in U.S. Pat. No. 4,784,950), as well as wild-type Factor VII derived from other species, such as, e.g., bovine, porcine, canine, murine, and salmon, said Factor VII derived from blood or plasma, or produced by recombinant means. It further encompasses natural allelic variations of Factor VII that may exist and occur from one individual to another. Also, the degree and location of glycosylation or other post-translation modifications may vary depending on the chosen host cells and the nature of the host cellular environment. The term "Factor VII" is also intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

As mentioned, the term "Factor VII polypeptides" is also denoted to mean "Factor VII-related polypeptides" The term "Factor VII-related polypeptides" are intended to encompass such polypeptides in their uncleaved (zymogen) form, as well as those that have been proteolytically processed to yield their respective bioactive forms. As used herein, "Factor VII-related polypeptides" encompass, without limitation, polypeptides exhibiting substantially the same or improved biological activity relative to wild-type human Factor VII and polypeptides wherein the biological activity has been substantially reduced relative to the activity of wild-type human factor VIIa (as disclosed in U.S. Pat. No. 4,784,950). These polypeptides include, without limitation, Factor VII or Factor VIIa that has been chemically modified, such as, e.g., by reacting factor VII with an irreversible inhibitor such as an organophosphor compound, a sulfonyl fluoride, a peptide halomethyl ketone or an azapeptide, or by acylation, by non-limiting example, and Factor VII variants into which specific amino acid sequence alterations have been introduced that slightly modify or improve the biological activity of the polypeptide, such as, e.g., polypeptides wherein the catalytic activity of factor VIIa is inhibited by chemical derivatization of the catalytic site, or triad.

The term "catalytic site" or "active site", when used herein with reference to FVIIa, refer to the catalytic and zymogen substrate binding site, including the "$S_1$" site of FVIIa as that term is defined by Schecter, I. and Berger, A., (1967) Biochem. Biophys. Res. Commun. 7:157-162. The catalytic site of human and bovine Factor VII proteins comprises the amino acids Ser344, Asp242, and His193 (subscript numbering indicating position in the sequence) that are forming a so-called catalytic "triad". The catalytic sites in Factor VII from other mammalian species may be determined using presently available techniques including, among others, protein isolation and amino acid sequence analysis. Catalytic sites may also be determined by aligning a sequence with the sequence of other serine proteases, particularly chymotrypsin, whose active site has been previously determined (Sigler et al., J. Mol. Biol., 35:143-164 (1968)) and therefrom determining from said alignment the analogous active site residues.

Factor VII-related polypeptides, including variants, having substantially the same or improved biological activity relative to wild-type Factor VIIa encompass those that exhibit at least about 25%, preferably at least about 50%, more preferably at least about 75%, more preferably at least about 100%, more preferably at least about 110%, more preferably at least about 120%, and most preferably at least about 130% of the specific activity of wild-type Factor VIIa that has been produced in the same cell type, when tested in one or more of a clotting assay, proteolysis assay, or TF binding assay as described in the present specification.

Factor VII-related polypeptides, including variants, wherein the biological activity has been substantially reduced relative to the activity of wild-type human factor VIIa encompass those polypeptides that exhibit less than about 25%, more preferably less than about 10%, or 5%, or 3%, or 2%, and most preferably less than about 1% of the specific activity of wild-type factor VIIa, when tested in one or more of a clotting assay, FIXa or FXa generation assay, amidolysis or proteolysis assay as described within the present specification In some embodiments the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see Examples, General Methods, below); in other embodiments the ratio is at least about 2.0; in further embodiments, the ratio is at least about 4.0. In some embodiments of the invention, the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Proteolysis Assay" (see Examples, General Methods, below); in other embodiments, the ratio is at least about 2.0; in further embodiments, the ratio is at least about 4.0; in further embodiments, the ratio is at least about 8.0.

Non-limiting examples of Factor VII variants having substantially the same or improved biological activity as wild-type Factor VII include S52A-FVII, S60A-FVII (Lino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS) and WO 04/029091 (Maxygen ApS); FVII variants having increased biological activity compared to wild-type FVIIa as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.).

Non-limiting examples of factor VII polypeptides having substantially reduced biological activity relative to wild-type factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and factor VIIa lacking the Gla domain, (Nicolaisen et al., FEBS Letts. 317: 245-249, 1993). Non-limiting examples also include human FVIIa, which has the lysine residue in position 341 replaced by another amino acid residue; human FVIIa, which has the serine residue in position 344 replaced by another amino acid residue; human FVIIa, which has the aspartic acid residue in position 242 replaced by another amino acid residue; human FVIIa, which has the histidine residue in position 193 replaced by another amino acid residue; FVII-(K341A); FVII-(S344A); FVII-(D242A); FVII-(H193A); Phe-Phe-Arg-FVII (FFR-FVII), D-Phe-Phe-Arg-FVII (D-FFR-FVII), Phe-Pro-Arg-FVII (FPR-FVII), D-Phe-Pro-Arg-FVII (D-FPR-FVII), L-Glu-Gly-Arg-FVII (EGR-FVII) and D-Glu-Gly-Arg-FVII (D-EGR-FVII), Dansyl-Phe-Phe-Arg-FVII, Dansyl-D-Phe-Phe-Arg-FVII, Dansyl-Phe-Pro-Arg-FVII, Dansyl-D-Phe-Pro-Arg-FVII, Dansyl-L-Glu-Gly-Arg-FVII and Dansyl-D-Glu-Gly-Arg-FVII. Non-limiting examples of chemically modified factor VII polypeptides and sequence variants are described, e.g., in U.S. Pat. No. 5,997,864.

Examples of factor VII or factor VII-related polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M 298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M 298Q-FVII, F374Y/V158D/S314E/E296V-FVII, F374Y/V158D/M 298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M 298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A/S314E-FVII, F374Y/V158T/E296V/K337A/S314E-FVII, F374Y/L305V/V158T/

K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M 298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M 298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

For purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) Measuring the ability of Factor VIIa or a Factor VIIa-related polypeptide to produce activated Factor X (Factor Xa) in a system comprising TF embedded in a lipid membrane and Factor X. (Persson et al., J. Biol. Chem. 272:19919-19924, 1997);

(ii) Measuring Factor X hydrolysis in an aqueous system ("In Vitro Proteolysis Assay", see Examples, General Methods, below);

(iii) Measuring the physical binding of Factor VIIa or a Factor VIIa-related polypeptide to TF using an instrument based on surface plasmon resonance (Persson, FEBS Letts. 413:359-363, 1997); and (iv) Measuring hydrolysis of a synthetic substrate by Factor VIIa and/or a Factor VIIa-related polypeptide ("In Vitro Hydrolysis Assay", see Examples, General Methods, below); and (v) Measuring generation of thrombin in a TF-independent in vitro system.

The term "Factor VII biological activity" or "Factor VII activity" is intended to include the ability to generate thrombin; the term also includes the ability to generate thrombin on the surface of activated platelets in the absence of tissue Factor.

"Examples, General Methods" of the present specification describes in detail assays useful for assaying FVII biological activity.

Moreover, throughout the present specification, the terms below have the following meaning:

The term "kit" or "kit of parts" is intended to mean a combination of a dry product, in a first unit, containing a polypeptide and one or more stabilizing agents; and an administration vehicle consisting of a solvent suitable for dissolving the dry product of the first unit, in combination with at least one buffering agent in an amount of from about from about 0.1 mM to 100 mM, and/or at least one tonicity modifying agent, in a second unit. The kit contains a pharmaceutical treatment, particularly of bleeding episodes. Before use, the dry composition of the first unit is mixed with and dissolved in the administration vehicle contained in the second unit, thereby providing a medicament ready for use.

The medicament ready for use is essentially isotonic.

The term "administration vehicle" is intended to encompass pharmaceutically acceptable, preferably sterile liquids suitable for administration by injectable means, such as infusion or injection, e.g., by intravenous, subcutaneous, or intramuscular injection. The administration vehicle is preferably aqueous. The administration vehicle comprises a solvent, or a mixture of solvents, suitable for reconstitution (solution) of the polypeptide composition (e.g., Water for Injection/WFI), and one or more agents suitable for keeping the pH of said composition in the range of 3 to 9 when dissolved in aqueous solvent in an amount of from about 0.1 mM to 100 mM; and/or one or more tonicity modifying agents in an amount sufficient to make essentially isotonic the reconstituted solution resulting from dissolving the composition of the first unit form in the administration vehicle of the second unit form.

The administration vehicle may contain further substances, such as metal salts, e.g., calcium and/or magnesium salts, amino acids, e.g., glycylglycine.

The reconstituted compositions are intended for parenteral administration for prophylactic and/or therapeutic treatment.

An "effective amount" of a polypeptide refers to the amount of polypeptide which, when administered in accordance with the invention, produces a measurable improvement in at least one clinical parameter of haemostasis known to those of ordinary skill in the art.

It will be understood that an effective amount of a polypeptide may vary according to the subject's haemostatic status, which, in turn, may be reflected in one or more clinical parameters, including, e.g., relative levels of circulating coagulation factors; amount of blood lost; rate of bleeding; hematocrit, and the like. It will be further understood that the single-dose-effective amount may be determined by those of ordinary skill in the art by routine experimentation, by constructing a matrix of values and testing different points in the matrix.

The term "stabilizing" is intended to encompass minimising the formation of aggregates (insoluble and/or soluble) and/or chemical degradation as well as providing maintenance of pH and proper conformation of the polypeptide during storage or production of the compositions so that substantial retention of biological activity and polypeptide stability is maintained. Moreover, stabilising is also denoted to mean lyoprotection and cryoprotection of the polypeptide during production of the compositions at freeze-drying conditions.

The term "stabilizing agent" is intended to encompass substances, or a mixture of substances, that are able to stabilize a polypeptide during storage or production of a composition comprising the polypeptide.

The term "structural stabilisation" or "structural stability" is intended to encompass the ability to form a lyophilised plug or cake with good properties and looks, e.g. such that it does not collapse and is readily dissolved before use.

The term "storage-stable" is intended to define a product that is stabilised upon storage at temperatures between 5° C.-40° C. and remains within pre-selected product specifications for a suitable time period—often several months.

The term "physical stability" of Factor VII polypeptides relates to the formation of insoluble and/or soluble aggregates in the form of dimeric, oligomeric and polymeric forms of Factor VII polypeptides as well as any structural deformation and denaturation of the molecule.

The term "chemical stability" is intended to relate to the formation of any chemical change in the Factor VII polypeptides upon storage in dissolved or solid state at accelerated conditions. By example are hydrolysis, deamidation and oxidation. In particular, the sulphur-containing amino acids are prone to oxidation with the formation of the corresponding sulphoxides.

The term "cryoprotectants" as used herein generally include agents, which provide stability to the polypeptide from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations.

The term "lyoprotectant" as used herein includes agents that provide stability to the polypeptide during water removal upon the drying process of the lyophilisation process. For example by maintaining the proper conformation of the polypeptide. Examples of lyoprotectants include saccharides, in particular di- or trisaccharides. Cryoprotectants may also have lyoprotectant effects.

The term "agent suitable for keeping the pH in the range of 3 to 9", or "buffering agent", encompasses those agents that maintain the solution pH in an acceptable range between 3.0 and 9.0. Typical examples of agents capable of keeping the pH within a range of 3 to 9 are the acid form or salts of citric acid, acetic acid, histidine, malic acid, phosphoric acid, tartaric acid, succinic acid, MES, HEPES, PIPES, imidazole, TRIS, lactic acid, glutaric acid and glycylglycine. It is to be understood that a combination of agents, wherein the combination of agents is suitable for maintaining the pH in the above-described range, may also be used in the present invention.

The term "lyophilised cake" as used herein is denoted to encompass the solid composition obtained upon processing a dissolved or at least a partly dissolved composition under conditions involving at least one step of cooling said dissolved/partly dissolved composition to ice followed by at least one step of vacuum drying.

The term "lyophilization" and "freeze-drying" encompasses a process during which liquid is removed from a dissolved or at least partly dissolved composition under conditions involving at least one step of cooling the dissolved or partly dissolved solution to ice followed by vacuum drying. Lyophilization, or freeze-drying, is the most common process for making solid polypeptide pharmaceuticals. The process consists of two major steps: freezing of a polypeptide solution, and drying of the frozen solid under vacuum. The drying step is further divided into two phases: primary and secondary drying. The primary drying removes the frozen water (sublimation of ice) and the secondary drying removes the non-frozen "bound" water (desorption of water). More detailed analysis of each lyophilization step is provided in, e.g., Wang et al, International journal of Pharmaceutics 203 (2000): 1-60 (see section 4, page 16 ff.).

Typically, a composition is freeze-dried by filling into vials, freezing on the shelves of the freeze-dryer, after which a vacuum is established and the shelves heated to implement primary drying (or sublimation of ice). Thereafter, secondary drying (or desorption of sorbed water) takes place at a higher temperature until the completion of the process, i.e., where the composition contains a sufficiently low content of moisture (water). Methods for freeze-drying are generally known in the art, see, for example, Wang et al, International journal of Pharmaceutics 203 (2000): 1-60.

It is within the ordinary skill of the practitioner to optimize the freeze-drying conditions in regard of temperature(s), time(s) at each temperature, and also pressure that is to be used during the process for a specific composition.

The term "moisture content" is meant to encompass water associated with the product, including, without limitation, water in adsorbed form, such as unfrozen water entrapped in or adsorbed to the frozen solute phase and/or associated with the amorphous phase or adsorbed to the crystalline solid. The term "water content" is used interchangeably with "moisture content". The desired residual moisture level (moisture content) is a function of the duration and the temperature of the secondary drying step. Several methods for determining the residual moisture content during lyophilization are known in the art; for example, an electronic hygrometer or a residual gas analyser may be used. Moisture contents of freeze-dried formulations can be determined by several methods known in the art, such as, for example, loss-on-drying, Karl Fischer titration, thermal gravimetric analysis (TGA), gas chromatography (GC), or near IR (see, e.g. Wang et al, International Journal of Pharmaceutics 203 (2000): 1-60). Methods for determining water contents (moisture contents) are also described in both the European and U.S. Pharmacopoeias. For example, determination of water content can be performed by Karl Fischer coulometric titration as described in the U.S. Pharmacopoeia (USP <921, Ic>) or the European Phamacopoeia (EP <2.5.32>).

In brief, the method is as follows:
Determination of Water Content by Coulometric Titration:

The Karl Fischer reaction is used in the coulometric determination of water based upon the quantitative reaction of water with sulphur dioxide and iodine in an anhydrous medium. Iodine is produced electrochemically in the reaction cell by oxidation of iodide. The iodine produced at the anode reacts immediately with the water and the sulphur dioxide contained in the reaction cell. The amount of water in the substance is directly proportional to the quantity of electricity up until the titration end-point. When all of the water in the cell has been consumed, the end-point is reached and thus an excess of iodine appears which is detected electrometrically thus indicating the end-point. The percentage water content present in the substance is then calculated.

Moisture content may be defined in terms of the weight of the sample in the vial at the time of analysis (i.e. solids plus the water present—called wet weight basis) or it may be defined in terms where it is corrected for the measured water in the sample (i.e. dry weight basis). In case of freeze-dried products with low moisture contents the two measurements (wet weight basis vs. dry weight basis) yield very similar results. As used herein, moisture contents are defined in terms of the solids plus the water present (i.e., wet weight basis).

The term "bulking agent" generally includes agents, which provide good lyophilised cake properties, which form a pharmaceutically elegant product, which help the polypeptide overcome various stresses, shear/freezing for example, associated with lyophilisation processes, and which help to maintain polypeptide activity levels during the freeze-drying process and subsequent storage. Non-limiting examples of bulking agents include mannitol, glycine, sucrose, lactose. These agents may also contribute to the tonicity of the formulations.

Isotonic solutions have a tonicity within the physiological range of the blood, peritoneal fluid or other relevant body fluids. By isotonicity is meant a solution with an osmotic pressure corresponding to the osmotic pressure of a 0.9%

NaCl solution (=286 mOsM). The term "essentially isotonic" is denoted to mean a tonicity corresponding to the osmotic pressure of a saline solution containing from about 0.7 to about 1.5% NaCl, such as, e.g., from about 0.8 to about 1.3%, about 0.8 to about 1.1%, about 0.8 to about 1.0%, or about 0.9% NaCl.

The term "tonicity modifier" or "tonicity modifying agent" is denoted to mean any agent, or mixture of agents, capable of adjusting the tonicity of the composition such that upon dissolving the composition at the time of use, the dissolved (or reconstituted) composition is essentially isotonic. Obviously, the tonicity of the reconstituted solution may depend on both the contents of tonicity-modifying agents in the dry composition and in the reconstitution solution.

Tonicity modifying agents include, without limitation, components selected from the list of: sodium acetate, sodium lactate, sodium chloride, potassium chloride, calcium chloride, mannitol, glycerol, propylene glycol, or mixtures of two or more of these.

Amounts of the above tonicity modifying agents suitable for providing a composition having a tonicity as defined above are, for example, from 0 to about 9 mg/ml of sodium chloride, from 0 to about 17 mg/ml of calcium chloride dihydrate, from 0 to about 51 mg/ml of mannitol, from 0 to about 26 mg/ml of glycerol, from 0 to about 21 mg/ml of propylene glycol, depending on whether the individual tonicity modifier is used alone or in combination with one or more tonicity modifiers.

The term "surfactants" generally include those agents, which protect the polypeptide from air/solution interface-induced stresses and solution/surface induced-stresses. For example surfactants may protect the polypeptide from aggregation. Suitable surfactants may include e.g. polysorbates, polyoxyethylene alkyl ethers such as Brij 35®, or poloxamer such as Tween 20, Tween 80, or poloxamer 188. Preferred surfactants are poloxamers, e.g. Poloxamer 188, Poloxamer 407; polyoxyethylene alkyl ethers, e.g. Brij 35®, Cremophor A25, Sympatens ALM/230; and polysorbates/Tweens, e.g. Polysorbate 20, Polysorbate 80. More preferred are Poloxamers, e.g. Poloxamer 188, and Tweens, e.g. Tween 20 and Tween 80. Typically, the surfactants are added in an amount of from 0.005 to 5 mg/ml. Preferred amounts are from 0.01 to 3 mg/ml, more preferred from 0.01 to 0.3 mg/ml for Tween 20 and/or Tween 80 and from 0.05 to 3.0 mg/ml for Poloxamer 188.

The term "initial content" relates to the amount of Factor VII polypeptides added to a composition at the time of preparation. The concentration given herein (mg/ml) refer to either the concentration in the solution of Factor VII polypeptide before removing the moisture (e.g. before freeze-drying) or in the reconstituted composition, or is referred as % w/w, which then relates to the concentration in the solid composition, e.g. the lyophilised cake.

As used herein, amounts specified are understood to be ±about 10%; thus about 50 mM includes 50 mM±5 mM, 4% includes 4%±0.4%, etc.

As stated above, the present investigators have contributed essentially to the art by stabilising Factor VII polypeptides thereby allowing long-term storage without causing increased risk and inconvenience to the user.

The present investigators have found that a number of crucial parameters need to be adjusted in stabilising Factor VII polypeptides. One important parameter relates, at least in part, to the moisture content, e.g. water. The moisture content should be limited. As a further essential parameter, the composition should at least include one stabilizing agent.

Stabilizing agents include, without limitation, antioxidants, saccharides, polyols, surfactants, and agents suitable for maintaining pH in a predetermined range.

In one embodiment of the present invention, a proper stabilizing agent includes the combination of at least two groups of pharmaceutically acceptable excipients selected from the group consisting of antioxidants, saccharides and polyols. The saccharides and polyols have lyoprotectant and/or cryoprotectant properties that may be important, at least in part, in the event where the composition is freeze-dried. In general, improved stability may be achieved, in part, by the proper combination of at least two of these groups of excipients. However, more specifically it was found that when said combination comprises a saccharide (sucrose) or an antioxidant (methionine), the stabilising effect may be even more significant. Moreover, it was also surprisingly found that methionine prevents oxidative degradation of the Factor VII polypeptides.

As stated, in one embodiment of the invention the stabilising agent includes combining at least two groups of pharmaceutically acceptable excipients.

According to the invention, the Factor VII polypeptide is meant to encompass the polypeptides as described above. In suitable embodiments of the invention, the Factor VII polypeptide is selected from the group consisting of Human Factor VIIa, Recombinant Human Factor VIIa and a Factor VII Sequence Variant. Preferably, the Factor VII Polypeptide is Human Factor VIIa or Recombinant Human Factor VIIa or a Factor VII-related polypeptide wherein the ratio between the activity of said Factor VII-related polypeptide and wild-type Factor VII is at least 1.25 when tested in one or more of the "In Vitro Proteolysis Assay" and the "in Vitro Hydrolysis Assay" as described in the present specification.

As stated, the moisture content should be limited. For the purposes of the present invention, the Factor VII polypeptides, when provided in bulk, may be provided in solid or liquid form. However, typically the Factor VII polypeptides, when provided in bulk, are in liquid form. Thus, further processing of the bulk polypeptides for the manufacturing of compositions requires the steps of adding suitable excipients and removing the liquid from the bulk, said addition of excipients may be carried out before or after removing the liquid. One such mean for removing liquid from a polypeptide relates to freeze-drying. Therefore, in a preferred embodiment of the present invention, the composition is in the form of a lyophilised cake. However, the present invention does not preclude other processes that are suitable for removing the liquid from the bulk polypeptide so as to achieve a solid composition with moisture content of not more than about 3% w/w.

Moreover, according to the invention, the moisture content is preferably not more than about 2.5% w/w, preferably not more than about 2% w/w, most preferably not more than about 1.5% w/w.

As may be understood, the invention relates, in part, to limiting the degradation of Factor VII polypeptides during preparation, e.g. during admixing of excipients and removing of liquid so as to achieve a solid composition with moisture content of the most 3% w/w, and to limiting said degradation from the time of manufacturing the solid composition until the time of use, e.g. until the time when the composition is to be administered by a patient.

Therefore, as a still further parameter in stabilising kits and compositions comprising Factor VII polypeptides, the pH should be kept in the pH range within 3 to 9 when dissolved in aqueous solvent, such as, e.g., pure water or aqueous buffer. That is to say that the pH in the polypeptide solution at the time before removing the moisture content, e.g. before freeze-drying, should be kept within a pH of about 3 to about 9. Advantageously, this pH range is also within the desired physiological range, thereby causing no harm to the user upon administering the composition by parenteral means. Preferably, the pH of the solution is from about 4.0 to about 9.0, such as 4.0 to 8.0, 4.0 to 7.5, 4.0 to 7.0, 4.5 to 7.0, 4.5 to 6.8, 4.5 to 6.5, 5.0 to 7.0, 5.0 to 6.5, 5.0 to 6.0, 5.5 to 6.0, or about 5.5 to about 6.5 such as about 5.5, 5.6, 5.7, 5.8, 5.9, 6.0, 6.1, 6.2, 6.3, 6.4, or 6.5.

In suitable embodiments of the invention, the agent suitable for keeping the pH in the range of 3 to 9 is selected from the group consisting of acid or salts of citric acid, acetic acid, histidine, malic acid, phosphoric acid, tartaric acid, succinic acid, MES, HEPES, imidazole, TRIS, lactic acid, glutaric acid, PIPES and glycylglycine, or a mixture of at least two such listed agents, wherein the mixture is able to provide a pH value in the specified range.

Furthermore, the suitable agent for keeping the pH in the range of 3 to 9 may also be a mixture of at least two such listed agents, wherein the mixture is able to provide a pH value in the specified range. The concentration of the suitable agents is in the range of from about 0.1 mM to 100 mM; from about 0.1 mM to about 50 mM; such as from about 0.1 mM to about 40 mM; from about 0.1 mM to about 35 mM; from about 0.1 mM to about 30 mM; from about 0.5 mM to about 25 mM; from about 1 mM to about 20 mM; from about 1 mM to about 15 mM; from about 5 mM to about 20 mM; or from about 5 mM to about 15 mM.

In one embodiment of the invention, the agent suitable for keeping the pH in the range of 3 to 9 is histidine, preferably L-histidine.

Degradation of the Factor VII polypeptide by the oxidative pathway as well as by the aggregation pathway are sensitive parameters of stability.

Typically, the compositions are stabilised upon termination of the freeze-drying such that less than 5% w/w, such as less than 4, 3 or 2% w/w of the initial content of Factor VII polypeptide is converted into its oxidised forms. The initial content of said Factor VII polypeptide being the amount added to the composition upon preparation of the composition before the freeze-drying step. Moreover, less than 5% w/w, such as less than 4.0%, 3.0%, 2.5%, 2%, 1.5%, or less than 1% w/w of the initial content of Factor VII polypeptide is recovered as aggregate forms, as determined by conventional analytical methods (such as, for example, as described in the Examples of the present application).

The present investigators have found that further degradation (i.e., as calculated from the time of termination of the manufacturing process until 8 months of storage at 30° C.) of a Factor VII polypeptide is minimal upon storage under ambient conditions. It was found that compositions comprising an antioxidant (methionine) are more stable towards oxidative degradation of the Factor VII polypeptide.

Therefore, suitable compositions have a limited increase in the content of oxidised forms upon storage for at least 8 months at ambient conditions.

That is to say that in still more interesting embodiments, the composition is stable such that no more than about 6% w/w of the initial content of Factor VII polypeptide is additionally degraded into oxidised forms upon storage of the composition for 8 months at 30° C. after termination of the manufacturing process, e.g. freeze-drying process. In further suitable embodiments thereof, not more than about 5, 4, 3, 2, or 1.5% w/w or of the Factor VII polypeptide is additionally converted into oxidised forms, as calculated from the time of termination of the manufacturing process until 8 months of storage at 30° C. In these embodiments of the invention the compositions are stable such that not more than about 5% (4, 3, 2, or 1.5%) w/w of the initial content of Factor VII polypeptide is converted to oxidised forms upon storage of said composition at 30° C. for 8 months. As stated above, the initial content relates to the amount of Factor VII polypeptide added to the composition upon preparation of the composition before the freeze-drying step.

As indicated, the degradation of Factor VII polypeptides by the aggregation pathway may also be regarded as an essential stability indicating parameter.

Thus, interesting embodiments of the invention relate to compositions that are stable such that not more than about 5% w/w of the initial content of Factor VII polypeptide is converted to aggregates upon storage of said composition at 30° C. for 8 months. As stated above the initial content of said Factor VII polypeptide being the amount added to the composition upon preparation of the composition before the freeze-drying step. By proper optimisation of, at least in part, the contents of saccharides, polyols and antioxidants, the composition is stable such that not more than about 4.0%, 3.0% w/w, such as 2.5, 2.0, 1.5, or 1.0% w/w, of the initial content of Factor VII polypeptide is converted to aggregates upon storage of said composition at 30° C. for 8 months.

Thus, advantageously, the compositions of the invention have low contents of oxidised forms and aggregates upon termination of the manufacturing process, i.e. upon termination of the freeze-drying process, and thus the compositions according to the invention are characterised by having a low initial content of oxidised forms and aggregates before being subjected to storage, e.g. not more than about 5% w/w, such as 4%, 3%, or 2% w/w of the initial contents of Factor VII polypeptide is converted into an oxidised form, and less than 5% w/w, such as not more than about 4.0%, 3.0%, 2.5%, 2%, 1.5%, or not more than about 1% w/w, is converted into a dimeric or higher-order polymeric form upon termination of the manufacturing process Moreover and advantageously, the kits and compositions of the invention are storage-stable, e.g. less than 10% w/w, such as 6%, 5%, 4%, 3%, 2%, or 1.5% w/w of the initial contents of Factor VII polypeptide is converted into an oxidised form, and less than 5% w/w, such as 4%, 3%, 2.5%, 2%, 1.5%, or 1% w/w is converted into a dimeric or higher-order polymeric form upon storage at 30° C. for at least 8 months in the dark.

As mentioned, said improved stability relates to the proper combination of particular excipients. According to the present invention, the stabilising agents may be selected from the group of saccharides, polyols and antioxidants. In suitable embodiments, the saccharides of interest are di- and tri-saccharides and polysaccharides such that the saccharides may be selected from the group consisting of sucrose, dextrose, lactose, maltose, trehalose, cyclodextrins, maltodextrins and dextrans. Moreover, in some embodiments, the polyol is selected from the group consisting of mannitol, sorbitol and xylitol. In still interesting embodiments, the antioxidant is selected from the group consisting of homocysteine, cysteine, cystathionine, methionine, gluthatione, and peptides containing any one of homocysteine, cysteine, cystathionine, methionine and gluthatione.

It is understood that the saccharide and polyol excipients, respectively, may also be a mixture of at least two such listed agents. In one series of embodiments of the invention, the saccharide excipient used is a combination of at least two di-, tri- and/or polysaccharides, such as, for example, sucrose in combination with cyclodextrin, trehalose in combination with cyclodextrin, sucrose in combination with dextran, or sucrose in combination with lactose. In one series of embodiments of the invention, the polyol excipient used is a combination of at least two polyols, such as, for example, mannitol in combination with sorbitol, mannitol in combination with xylitol, or sorbitol in combination with xylitol. In one series of embodiments of the invention, the antioxidant excipient used is a combination of at least two antioxidants, such as, for example, methionine in combination with one or more of homocysteine, cysteine, cystathionine, gluthatione, and peptides containing any one of homocysteine, cysteine, cystathionine, methionine and gluthatione.

In particular interesting embodiments, the antioxidant is selected from the group consisting of homocysteine, cysteine, cystathionine, methionine, gluthatione, and peptides containing any one of homocysteine, cysteine, cystathionine, methionine and gluthatione. In a preferred embodiment, the antioxidant is methionine.

In further interesting embodiments of the invention, the polyols are to be present in an amount ranging from about 5% w/w to about 90% w/w. Preferably, the amount of the polyol is to be present in a range from about 18% w/w to about 88% w/w, such as from about 18% w/w to about 83% w/w, 25% to 80%, 30% to 65%, 30% to 80%, 40% to 80%, 50% to 80%, 30% to 75%, 40% to 75%, 50% to 75%, or from about 50% to about 70% w/w.

The polyol are to be present in an amount ranging from about 0.5 to 75 mg/ml, such as from about 2 to 60 mg/ml, 5 mg/ml to 55 mg/ml, 8 to 45 mg/ml, 10 to 40 mg/ml, 10 to 30 mg/ml, or from about 2 to 45 mg/ml, 5 mg/ml to 45 mg/ml, 5 to 35 mg/ml, 5 to 25 mg/ml, 5 to 20 mg/ml, 20 to 40 mg/ml, or such as from about 20 to 30 mg/ml, Moreover, in interesting embodiments thereof as well as in some other interesting embodiments of the invention, the saccharide is to be present in the composition in an amount ranging from about 0 to about 85% w/w. In further interesting embodiments thereof, the amount ranges from about 3% w/w to about 80% w/w, such as from about 7% w/w to about 75% w/w, 10% to 70%, 10% to 50%, 20% to 50%, 10% to 40%, or from about 10% w/w to about 35% w/w.

The saccharide should be in an amount ranging from about 0.5 to 75 mg/ml, such as from about 2 to 60 mg/ml, from about 5 mg/ml to 55 mg/ml, from about 8 to 45 mg/ml, from about 10 to 40 mg/ml, from about 10 to 30 mg/ml, or from about 2 to 45 mg/ml, from about 5 mg/ml to 45 mg/ml, from about 5 to 35 mg/ml, from about 5 to 25 mg/ml, such as from about 5 to 20 mg/ml.

The antioxidant should be provided in an amount ranging from about 0.05 to 10 mg/ml, preferably from about 0.1 to 5 mg/ml, more preferably from about 0.1 mg/ml to 2.5 mg/ml, even more preferably from about 0.1 to 2 mg/ml, most preferably from about 0.1 to 1 mg/ml.

The ratio between the polyol and the saccharide needs to be properly adjusted. In suitable embodiments of the invention, said polyol is in a weight ratio relative to said saccharide ranging from about 100:1 to 1:50. In even more suitable embodiments thereof, said weight ratio is from about 50:1 to 1:10, more preferably from about 20:1 to 1:5. In other suitable embodiments, the weight ratio relates to ranges from about 10:1 to 1:2, and from about 6:1 to 1:2. Suitable embodiments relate to those wherein said sugar alcohol is in a weight ratio relative to said saccharide ranging from about 4:1 to 1:1, such as from about 4:1 to 3:2 or from about 1:1 to 3:2.

In some embodiments of the invention, the polyol is mannitol and in still further embodiments the saccharide is sucrose. Moreover, in still further embodiments the antioxidant is methionine.

In still preferred embodiments of the invention, the composition further comprises other pharmaceutical excipients acting as bulking agent. That is to say that bulking agents other than mannitol are included in the compositions. In particular, bulking agents are included in compositions prepared by freeze-drying.

Initial contents of Factor VII polypeptide in the composition is preferably from about 0.6 mg/mL to about 10.0 mg/mL, such as from about 0.6 mg/mL to about 8 mg/mL, from about 0.6 mg/mL to about 6 mg/mL, from about 0.6 mg/mL to about 5 mg/mL, from about 0.6 mg/mL to about 4 mg/mL, from about 0.6 mg/mL to about 3 mg/mL, from about 1.0 mg/mL to about 5 mg/mL, from about 1.0 mg/mL to about 4 mg/mL, or from about 1.0 mg/mL to about 3 mg/mL, e.g., about 1.0 mg/mL, about 2.0 mg/mL, about 3.0 mg/mL, about 4.0 mg/mL, or about 5.0 mg/mL.

In one embodiment, the composition contained in the first unit form of the kit comprises: Factor VII polypeptide, Mannitol, Sucrose, and polysorbate, preferably polysorbate 20 or 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In one embodiment, the composition contained in the first unit form of the kit comprises: Factor VII polypeptide, Mannitol, Sucrose, methionine, and polysorbate, preferably polysorbate 20 or 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition contained in the first unit form of the kit comprises Factor VII polypeptide, Mannitol, Sucrose, Histidine, and polysorbate, preferably polysorbate 20 or 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In one embodiment, the composition contained in the first unit form of the kit comprises: Factor VII polypeptide, Mannitol, Sucrose, methionine, Histidine, and polysorbate, preferably polysorbate 20 or 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition contained in the first unit form of the kit comprises Factor VII polypeptide, Mannitol, Sucrose, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition contained in the first unit form of the kit comprises Factor VII polypeptide, Mannitol, Sucrose, methionine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition contained in the first unit form of the kit comprises Factor VII polypeptide, Mannitol, Sucrose, Histidine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition contained in the first unit form of the kit comprises Factor VII polypeptide, Mannitol, Sucrose, Histidine, methionine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In one embodiment, the administration vehicle contained in the second unit form of the kit comprises: Water, and histidine. In a further embodiment, the vehicle further comprises one or more components selected from the list of: CaCl2, NaCl, and Glycylglycine. In a further embodiment thereof, the vehicle comprises one or more components selected from the list of: CaCl2 in a concentration of about 5-15 mM, NaCl in a concentration of about 30 to 60 mM, such as, e.g., about 40 mM or about 50 mM.

In a preferred embodiment, the method for preparing a stable Factor VII polypeptide comprises freeze-drying. The freeze-drying relates to a process, wherein the solution comprising said Factor VII polypeptide is filled into lyophilisation vials or the like. Said Factor VII polypeptide may optionally be subjected to sterile filtration before start of freeze-drying. Cooling is applied to the shelves of the freeze-drier in order to freeze the vials and the solution below critical product temperatures. Water is removed by introducing vacuum and condensation of water vapour on the ice-condenser of the freeze-drier. When the product is dry, usually less than 3% residual moisture content (e.g., measured by Karl Fischer coulometric titration as described above), the vials are closed and capped. Manufacturing is finalised and the composition is now in a form of a lyophilised cake.

The reconstituted compositions are intended for parenteral administration for prophylactic and/or therapeutic treatment. Preferably, the pharmaceutical compositions are administered parenterally, i.e., intravenously, subcutaneously, or intramuscularly, or they are administered by way of continuous or pulsative infusion.

Therefore, a still further aspect of the invention relates to the use of the solid stabilised composition for the preparation of a medicament for treating a coagulation factor-responsive syndrome. In one embodiment, the invention relates to the use of Factor VII polypeptide for the preparation of a medicament for treating a Factor VII-responsive syndrome.

In different embodiments, said Factor VII-responsive syndrome is haemophilia A, haemophilia B, Factor XI deficiency, Factor VII deficiency, thrombocytopenia, von Willebrand's disease, presence of a clotting Factor inhibitor, surgery or trauma. Additionally, Factor VII-responsive syndrome may be associated with anticoagulant therapy.

As stated the compositions of the invention is in solid form. Accordingly, in a suitable embodiment the medicament should be suitable for being dissolved, which allows for parenteral administration of the medicament. Thus, when administering the compositions to a patient, it comprises the step of dissolving the composition in a suitable liquid prior to the administering step.

Abbreviations used herein:

FVII: Coagulation Factor VII in its single chain form

FVIIa: Coagulation Factor VII in its cleaved, activated two-chain form rFVII (rFVIIa): Recombinant Factor VII (recombinant Factor VIIa)

EMBODIMENTS

In one series of embodiments of the invention, the first unit form of the kit comprises the excipients, and amounts thereof, and has the pH as shown in the list of formulations 1 to 48:

TABLE 1

| Composition | 1 | 2 | 3 | 4 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 5 | 6 | 7 | 8 |
|---|---|---|---|---|
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 9 | 10 | 11 | 12 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 13 | 14 | 15 | 16 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |

TABLE 1-continued

| | | | | |
|---|---|---|---|---|
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | 17 | 18 | 19 | 20 |
|---|---|---|---|---|
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | 21 | 22 | 23 | 24 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | 25 | 26 | 27 | 28 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 29 | 30 | 31 | 32 |
|---|---|---|---|---|
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 33 | 34 | 35 | 36 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | 37 | 38 | 39 | 40 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | 41 | 42 | 43 | 44 |
|---|---|---|---|---|
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | 45 | 46 | 47 | 48 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

In another series of embodiments, the first unit form of the kit comprises the excipients, and amounts thereof, and has the pH as shown in the list of formulations 100 to 124:

TABLE 2

| Composition | 100 | 102 | 103 | 104 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |

TABLE 2-continued

| | | | | |
|---|---|---|---|---|
| Sucrose | 10 mg/mL | 10 mg/mL | 10 mg/mL | 10 mg/mL |
| pH | 5.50 | 5.50 | 5.50 | 5.50 |
| Composition | 105 | 106 | 107 | 108 |
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |
| Composition | 109 | 110 | 111 | 112 |
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |
| Composition | 113 | 114 | 115 | 116 |
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |
| Composition | 117 | 118 | 119 | 120 |
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |
| Composition | 121 | 122 | 123 | 124 |
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Poloxamer | 1.0 mg/mL | 1.0 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

In one series of embodiments, the concentration of FVII polypeptide in any one of compositions 1 to 48 and 100 to 124 is from about 0.6 mg/mL to about 10.0 mg/mL, such as from about 0.6 mg/mL to about 8 mg/mL, from about 0.6 mg/mL to about 5 mg/mL, from about 0.6 mg/mL to about 3 mg/mL, from about 1.0 mg/mL to about 5 mg/mL, or from about 1.0 mg/mL to about 3 mg/mL.

In another series of embodiments, the concentration of FVII polypeptide in any one of compositions 1 to 48 and 100 to 124 is selected from the list of: about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3.0 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, and about 4.0 mg/mL In one series of embodiments, the concentration of polysorbate in formulations 1 to 48 and 100 to 124 is from about 0.05 to 0.08 mg/mL, such as, from about 0.06 to 0.08 mg/mL, or about 0.07 mg/mL.

In a another series of embodiments, the first unit forms comprise a composition as described in any one of compositions 1 to 48 and 100 to 124, and the second unit form comprises L-histidine in an amount of from about 0.5 mg/mL to 3 mg/mL, such as, from about 1.0 to about 2.0 mg/mL, or about 1.55 mg/ML.

In yet another series of embodiments, the first unit forms comprise a composition as described in any one of compositions 1 to 48 and 100 to 124, and the second unit form comprises from about 30 to about 60 mM NaCl, such as, about 40 mM, about 45 mM, or about 50 mM NaCl.

In yet another series of embodiments, the first unit forms comprise a composition as described in any one of compositions 1 to 48 and 100 to 124, and the second unit form comprises from about 30 to about 60 mM NaCl, such as, about 40 mM, about 45 mM, or about 50 mM NaCl; and L-histidine in an amount of from about 0.5 mg/mL to 3 mg/mL, such as, from about 1.0 to about 2.0 mg/mL, or about 1.55 mg/ML.

Another aspect of the invention is the provision of novel compositions comprising a Factor VII polypeptide and at least one stabilizing agent selected from the group consisting of
a) a combination of an antioxidant and mannitol;
b) a combination of methionine and a polyol;
c) a combination of a saccharide and mannitol;
d) a combination of sucrose and a polyol;
e) methionine; and
a polysorbate surfactant in an amount of from about 0.06 to 0.08 mg/mL;
said composition having a moisture content of not more than about 3%;

In one embodiment, the combination of an antioxidant and mannitol (a) further comprises a saccharide. In another embodiment, the combination of methionine and a polyol (b) further comprises a saccharide. In another embodiment, the combination of a saccharide and mannitol (c) further comprises an antioxidant. In another embodiment, the combination of sucrose and a polyol (d) further comprises an antioxidant.

In an interesting embodiment, the antioxidant is selected from the group consisting of homocysteine, cysteine, cystathionine, methionine, gluthatione, and peptides containing any one of homocysteine, cysteine, cystathionine, methionine and gluthatione, or mixtures thereof; preferably methionine, or mixtures containing methionine. In another interesting embodiment, the saccharide is selected from the group consisting of sucrose, dextrose, lactose, maltose, trehalose, cyclodextrins, maltodextrins and dextrans, or mixtures thereof; preferably sucrose, or mixtures containing sucrose. In yet another interesting embodiment, the polyol is selected from the group consisting of mannitol, sorbitol and xylitol, or mixtures thereof; preferably mannitol, or mixtures containing mannitol.

The compositions may further comprise an agent suitable for keeping the pH of said composition in the range of 3 to 9 when dissolved in aqueous solvent. Non-limiting examples of such agents as well as preferred pH ranges have been described above.

The composition may further comprise a tonicity modifier. Non-limiting examples of such tonicity modifiers have been described above.

TABLE 3

| Compound | Formulation I | Formulation II |
|---|---|---|
| FVII polypeptide | 0.6 to 10 mg/ml | 0.6 to 10 mg/ml |
| Mannitol | 20 to 40 mg/ml | 20 to 40 mg/ml |
| Sucrose | 5 to 20 mg/ml | — |
| Methionine | 0-1 mg/ml | 0-1 mg/ml |
| Polysorbate | 0.01 to 0.09 mg/ml | 0.01 to 0.09 mg/ml |
| pH | 5.0 to 7.0 | 5.0 to 7.0 |

In one embodiment thereof, the compositions are selected from the list of:

TABLE 4

| Compound | Formulation III | Formulation IV |
|---|---|---|
| FVII polypeptide | 0.6 to 3.0 mg/ml | 0.6 to 3.0 mg/ml |
| Mannitol | 20 to 40 mg/ml | 20 to 40 mg/ml |
| Sucrose | 5 to 20 mg/ml | — |
| Methionine | 0-1 mg/ml | 0-1 mg/ml |
| Polysorbate | 0.01 to 0.09 mg/ml | 0.01 to 0.09 mg/ml |
| pH | 5.0 to 7.0 | 5.0 to 7.0 |

In one embodiment thereof, the compositions are selected from the list of:

TABLE 5

| Compound | Formulation V | Formulation VI | Formulation VII |
|---|---|---|---|
| FVII polypeptide | 0.6 to 3.0 mg/ml | 0.6 to 3.0 mg/ml | 0.6 to 3.0 mg/ml |
| Mannitol | 25 mg/ml | 25 mg/ml | 25 mg/ml |
| Sucrose | 10 mg/ml | — | 10 mg/ml |
| Methionine | 0-1 mg/ml | 0-1 mg/ml | 0.5 mg/ml |
| Polysorbate | 0.01 to 0.09 mg/ml | 0.01 to 0.09 mg/ml | 0.01 to 0.09 mg/ml |
| pH | 5.5 to 6.5 | 5.5 to 6.5 | 5.5 to 6.5 |

| Compound | Formulation VIII | Formulation IX | Formulation X |
|---|---|---|---|
| FVII polypeptide | 0.6 to 3.0 mg/ml | 0.6 to 3.0 mg/ml | 0.6 to 3.0 mg/ml |
| Mannitol | 25 mg/ml | 25 mg/ml | 25 mg/ml |
| Sucrose | — | 10 mg/ml | — |
| Methionine | 0.5 mg/ml | — | — |
| Polysorbate | 0.01 to 0.09 mg/ml | 0.01 to 0.09 mg/ml | 0.01 to 0.09 mg/ml |
| pH | 5.5 to 6.5 | 5.5 to 6.5 | 5.5 to 6.5 |

| Compound | Formulation XI | Formulation XII | Formulation XIII |
|---|---|---|---|
| FVII polypeptide | 0.6 to 1.5 mg/ml | 0.6 to 1.5 mg/ml | 0.6 to 1.5 mg/ml |
| Mannitol | 25 mg/ml | 25 mg/ml | 25 mg/ml |
| Sucrose | 10 mg/ml | — | 10 mg/ml |
| Methionine | 0-1 mg/ml | 0-1 mg/ml | 0.5 mg/ml |
| Polysorbate | 0.01 to 0.09 mg/ml | 0.01 to 0.09 mg/ml | 0.01 to 0.09 mg/ml |
| pH | 5.5 to 6.5 | 5.5 to 6.5 | 5.5 to 6.5 |

| Compound | Formulation XIV | Formulation XV | Formulation XVI |
|---|---|---|---|
| FVII polypeptide | 0.6 to 1.5 mg/ml | 0.6 to 1.5 mg/ml | 0.6 to 1.5 mg/ml |
| Mannitol | 25 mg/ml | 25 mg/ml | 25 mg/ml |
| Sucrose | — | 10 mg/ml | — |
| Methionine | 0.5 mg/ml | — | — |
| Polysorbate | 0.01 to 0.09 mg/ml | 0.01 to 0.09 mg/ml | 0.01 to 0.09 mg/ml |
| pH | 5.5 to 6.5 | 5.5 to 6.5 | 5.5 to 6.5 |

The polysorbate surfactant is selected from the group consisting of polysorbate 20 or 80, preferably polysorbate 80.

In one embodiment of the invention, the novel compositions are selected from the list of:

In one series of embodiments, the concentration of polysorbate in formulations I to XVI is from about 0.05 to 0.08 mg/mL, such as, from about 0.06 to 0.08 mg/mL, or about 0.07 mg/mL.

In one series of embodiments, the polysorbate in formulations I to XVI is polysorbate 20, e.g. Tween 20™. In one series of embodiments, the FVII polypeptide in formulations I to XVI is polysorbate 80, e.g., Tween 80™.

In yet another embodiment, the compositions are selected from the list of:

TABLE 6

| Compound | Formulation XVII | Formulation XVIII | Formulation XIX | Formulation XX |
|---|---|---|---|---|
| FVII polypeptide | 1.0 mg/ml | 1.0 mg/ml | 1.0 mg/ml | 1.0 mg/ml |
| Mannitol | 25 mg/ml | 25 mg/ml | 25 mg/ml | 25 mg/ml |
| Sucrose | 10 mg/ml | 10 mg/ml | 10 mg/ml | 10 mg/ml |
| Methionine | 0.5 mg/ml | — | 0.5 mg/ml | — |
| Tween 80 | 0.05 to 0.08 mg/ml | 0.05 to 0.08 mg/ml | 0.05 to 0.08 mg/ml | 0.05 to 0.08 mg/ml |
| pH | 6.0 | 6.0 | 5.5 | 5.5 |

| Compound | Formulation XXI | Formulation XXII | Formulation XXIII | Formulation XXIV |
|---|---|---|---|---|
| FVII polypeptide | 1.0 mg/ml | 1.0 mg/ml | 1.0 mg/ml | 1.0 mg/ml |
| Mannitol | 25 mg/ml | 25 mg/ml | 25 mg/ml | 25 mg/ml |
| Sucrose | 10 mg/ml | 10 mg/ml | 10 mg/ml | 10 mg/ml |
| Methionine | 0.5 mg/ml | — | 0.5 mg/ml | — |
| Tween 80 | 0.05 to 0.08 mg/ml | 0.05 to 0.08 mg/ml | 0.07 mg/ml | 0.07 mg/ml |
| pH | 6.5 | 6.5 | 5.5 | 5.5 |

| Compound | Formulation XXV | Formulation XXVI | Formulation XXVII | Formulation XXVIII |
|---|---|---|---|---|
| FVII polypeptide | 1.0 mg/ml | 1.0 mg/ml | 1.0 mg/ml | 1.0 mg/ml |
| Mannitol | 25 mg/ml | 25 mg/ml | 25 mg/ml | 25 mg/ml |
| Sucrose | 10 mg/ml | 10 mg/ml | 10 mg/ml | 10 mg/ml |
| Methionine | 0.5 mg/ml | — | 0.5 mg/ml | — |
| Tween 80 | 0.07 mg/ml | 0.07 mg/ml | 0.07 mg/ml | 0.07 mg/ml |
| pH | 6.0 | 6.0 | 6.5 | 6.5 |

In one series of embodiments, the formulations I to XXVIII further comprise one or more components selected from the list of:

Ca2+, preferably in an amount of from about 5 to about 15 mM, such as about 10 mM, and preferably as CaCl2×2H2O;

NaCl, preferably in an amount of about 50 mM, or about 40 mM, e.g., 39 mM;

Histidine, preferably L-Histidine, preferably in an amount of about 10 mM; and

Glycylglycine, e.g., in an amount of about 10 mM

In another series of embodiments, the compositions contain the excipients, and amounts thereof, as described in any one of Formulations I to XXVIII but has a pH of pH 5.5, or 5.6, or 5.7, or, 5.8, 5.9, or 6.1, or 6.2, or 6.3, or 6.4, or 6.5.

In one series of embodiments, the concentration of FVII polypeptide in formulations I to XVI is about 1.0 mg/mL.

In one series of embodiments, the FVII polypeptide in formulations I to XXVIII is wild-type human factor VIIa.

In one series of embodiments, the FVII polypeptide in formulations I to XXVIII is a FVII variant.

In different series of embodiments, the FVII polypeptide in formulations I to XXVIII is selected from the list of: L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII;

In different series of embodiments, the Factor VII polypeptide in any one of compositions 1 to 48 and 100 to 124 is selected from the list of: From about 0.6 mg/mL to about 10.0 mg/mL, such as from about 0.6 mg/mL to about 8 mg/mL, from about 0.6 mg/mL to about 6 mg/mL, from about 0.6 mg/mL to about 5 mg/mL, from about 0.6 mg/mL to about 4 mg/mL, from about 0.6 mg/mL to about 3 mg/mL, from about 1.0 mg/mL to about 5 mg/mL, from about 1.0 mg/mL to about 4 mg/mL, from about 1.0 mg/mL to about 3 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3.0 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, and about 4.0 mg/mL.

In another aspect, the invention provides a method of preparing the novel compositions defined in Tables 3 to 6, comprising the steps of:

i) providing a Factor VII polypeptide in a solution comprising at least one stabilizing agent selected from the group consisting of a) a combination of an antioxidant and mannitol;
b) a combination of methionine and a polyol;
c) a combination of a saccharide and mannitol;
d) a combination of sucrose and a polyol; and
e) methionine ii) processing said solution so as to obtain a solid composition with a moisture content not more than about 3% w/w.

In one embodiment, the polyol is present in an amount ranging from about 0.5 to about 75 mg/ml, preferably from about 2 to 45 mg/ml, such as from about 5 mg/ml to 45 mg/ml, from about 5 to 35 mg/ml, from about 5 to 25 mg/ml, 5 to 20 mg/ml, 20 to 40 mg/ml, or from about 20 to about 30 mg/ml, In one embodiment, the saccharide is present in an amount ranging from about 0.5 to 75 mg/ml, preferably from about 2 to 45 mg/ml, such as from about 5 mg/ml to 45 mg/ml, from about 5 to 35 mg/ml, from about 5 to 25 mg/ml, or from about 5 to 20 mg/ml.

In one embodiment, the antioxidant is in an amount ranging from about 0.05 to 10 mg/ml, preferably from about 0.1 to 5 mg/ml, more preferably from about 0.1 mg/ml to 2.5 mg/ml, even more preferably from about 0.1 to 2 mg/ml, most preferably from about 0.1 to 1 mg/ml.

In one embodiment, the saccharide is sucrose. In one embodiment, the antioxidant is methionine. In one embodiment, the polyol is mannitol. In one embodiment, the processing comprises freeze-drying.

The novel compositions of the present invention are reconstituted using an acceptable, preferably sterile, diluent or carrier, preferably an aqueous carrier. Non-limiting examples of aqueous carriers include Water for Injection (WFI) as well as solvents as described in the present specification (above) containing at least one of the components selected from the list of: (i) an agent suitable for keeping the pH of said composition in the range of 3 to 9 when dissolved in aqueous solvent in an amount of from about 0.1 mM to 100 mM; and (ii) a tonicity modifying agent in an amount sufficient to make essentially isotonic the reconstituted solution. In one embodiment, the carrier is WFI; in another embodiment, the solvent comprises histidine.

EMBODIMENTS OF THE INVENTION

Embodiment 1

A kit containing a pharmaceutical medicament, said kit comprising
a) a composition comprising a polypeptide and at least one stabilizing agent, wherein the composition has a moisture content of not more than about 3%, in a first unit form, and container means for containing said first unit form;
and,
b) in a second unit form, an administration vehicle comprising a solvent for reconstitution (solution) of said composition and at least one of the components selected from the list of:
(iii) an agent suitable for keeping the pH of said composition in the range of 3 to 9 when dissolved in aqueous solvent, wherein the agent is present in an amount of from about 0.1 mM to 100 mM,
(iv) a tonicity modifying agent in an amount sufficient to make essentially isotonic the reconstituted solution resulting from dissolving the composition of the first unit form in the administration vehicle of the second unit form;
and container means for containing said second unit form.

Embodiment 2

A kit in accordance with Embodiment 1, wherein the first unit form comprises at least one component selected from the group of: surfactants, antioxidants, saccharides, and polyols.

Embodiment 3

A kit in accordance with embodiment 2 or embodiment 2, wherein the second unit form further comprises at least one component selected from the group of: surfactants, antioxidants, saccharides, and polyols.

Embodiment 4

A kit in accordance with any one of embodiments 1 to 3, wherein the polypeptide is a blood coagulation factor, such as Factor VIII, Factor IX, Factor X, Factor II, Factor V, Factor VII.

Embodiment 5

A kit in accordance with any one of embodiments 1 to 3, wherein the polypeptide is a vitamin K-dependent polypeptide, such as Factor VII, Factor IX, Factor X, Factor II, Protein C, Protein S, prothrombin.

Embodiment 6

A kit in accordance with embodiments 4 or 5, wherein the coagulation factor polypeptide is selected from the list of: human Factor VIII, human Factor VIIa, a Factor VII-related polypeptide, human Factor IX, human Factor X, activated human Protein C.

Embodiment 7

A kit in accordance with embodiment 6, wherein the FVII-related polypeptide is a factor VII variant selected from the list of: L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII.

Embodiment 8

A kit in accordance with embodiment 6, wherein the FVII-related polypeptide is a factor VII variant wherein the ratio between the activity of said Factor VII variant and human factor VIIa (wild-type Factor VII) is at least 1.25 when tested in one or more of the "In Vitro Proteolysis Assay" and the "in Vitro Hydrolysis Assay" as described in the present specification.

Embodiment 9

A kit in accordance with any one of embodiments 1 to 8, wherein the "agent suitable for keeping the pH of said composition in the range of 3 to 9 when dissolved in aqueous solvent" is present in an amount of from about 0.1 mM to about 50 mM; such as from about 0.1 mM to about 40 mM; from about 0.1 mM to about 35 mM; from about 0.1 mM to about 30 mM; from about 0.5 mM to about 25 mM; from about 1 mM to about 20 mM; from about 1 mM to about 15 mM; from about 5 mM to about 20 mM; or from about 5 mM to about 15 mM.

Embodiment 10

A kit in accordance with any one of embodiments 1 to 9, wherein the "agent suitable for keeping the pH of said composition in the range of 3 to 9 when dissolved in aqueous solvent" is selected from the list of: citric acid, acetic acid, histidine, malic acid, phosphoric acid, tartaric acid, succinic acid, MES, HEPES, imidazole, TRIS, lactic acid, glutaric acid, PIPES and glycylglycine, or a mixture of at least two such listed agents, wherein the mixture is able to provide a pH value in the specified range.

Embodiment 11

A kit in accordance with any one of embodiments 1 to 10, wherein the second unit form comprises an agent suitable for keeping the pH of said composition in the range of 4 to 7 when dissolved in aqueous solvent; preferably in the range of 4.5 to 7.5, such as 5 to 7, or 5.5 to 6.5.

Embodiment 12

A kit in accordance with any one of embodiments 1 to 11, wherein the second unit form comprises histidine Embodiment 13

A kit in accordance with any one of embodiments 1 to 12, wherein the "tonicity modifying agent" is selected from the list of: Sodium acetate, sodium lactate, sodium chloride, potassium chloride, calcium chloride, mannitol, glycerol, propylene glycol, or a mixture of at least two such listed modifying agents; preferably selected from the list of: sodium chloride mannitol, glycerol, propylene glycol, calcium chloride, or mixtures thereof.

Embodiment 14

A kit in accordance with embodiment 13, wherein the tonicity modifying agent comprises Ca2+ or Mg2+.

Embodiment 15

A kit in accordance with any one of embodiments 1 to 14, wherein one or both of the first and second unit forms further contain a preservative.

Embodiment 16

A kit in accordance with any one of the preceding embodiments; wherein the first unit form comprises at least one stabilizing agent selected from the group consisting of
a) a combination of an antioxidant and mannitol;
b) a combination of methionine and a polyol;
c) a combination of a saccharide and mannitol;
d) a combination of sucrose and a polyol;
e) methionine; and
f) a surfactant
said composition having a moisture content of not more than about 3%.

Embodiment 17

A kit in accordance with embodiment 16, wherein the combination of an antioxidant and mannitol further comprises a saccharide.

Embodiment 18

A kit in accordance with embodiment 16, wherein the combination of methionine and a polyol further comprises a saccharide.

Embodiment 19

A kit in accordance with embodiment 16, wherein the combination of a saccharide and mannitol further comprises an antioxidant.

Embodiment 20

A kit in accordance with embodiment 16, wherein the combination of sucrose and a polyol further comprises an antioxidant.

Embodiment 21

A kit in accordance with any one of embodiments 16 or 17, wherein the combination of an antioxidant and mannitol (a) further comprises a surfactant Embodiment 22

A kit in accordance with any one of embodiments 16 or 18, wherein the combination of methionine and a polyol (b) further comprises a surfactant.

Embodiment 23

A kit in accordance with any one of embodiments 16 or 19, wherein the combination of a saccharide and mannitol (c) further comprises a surfactant.

Embodiment 24

A kit in accordance with any one of embodiments 16 or 20, wherein the combination of sucrose and a polyol (d) further comprises a surfactant.

Embodiment 25

A kit in accordance with embodiment 16, wherein the stabilizing agent is a combination of a surfactant and methionine (e).

Embodiment 26

A kit in accordance with any one of the preceding embodiments, wherein the antioxidant is selected from the group consisting of homocysteine, cysteine, cystathionine, methionine, gluthatione, and peptides containing any one of homocysteine, cysteine, cystathionine, methionine and gluthatione.

Embodiment 27

A kit in accordance with any one of the preceding embodiments, wherein the saccharide is selected from the group consisting of sucrose, dextrose, lactose, maltose, trehalose, cyclodextrins, maltodextrins and dextrans.

Embodiment 28

A kit in accordance with any one of the preceding embodiments, wherein the polyol is selected from the group consisting of mannitol, sorbitol and xylitol.

Embodiment 29

A kit in accordance with any one of the preceding embodiments, wherein the composition of the first unit form is stable such that not more than about 5% w/w of the initial content of Factor VII polypeptide is converted to aggregates upon storage of said composition at 30° C. for 8 months, preferably not more than about 4.0% w/w, 3.0% w/w, 2.5% w/w, 2.0% w/w, 1.5% w/w, or not more than about 1.0% w/w, Embodiment 30

A kit in accordance with any one of the preceding embodiments, wherein the composition of the first unit form is stable such that not more than about 6% w/w of the initial content of Factor VII polypeptide is converted to oxidised forms upon storage of said composition at 30° C. for 8 months, preferably not more than about 5% w/w, 4.0% w/w, 3.0% w/w, 2.5% w/w, 2.0% w/w, or not more than about 1.5% w/w.

Embodiment 31

A kit in accordance with any one of the preceding embodiments, wherein said polyol is in an amount ranging from about 5% w/w to 90% w/w, preferably from about 18% w/w to 88% w/w, 18% to 83%, 25% to 80%, 40% to 80%, 50% to 80%, or from about 50% w/w to 70% w/w.

Embodiment 32

A kit in accordance with any one of the preceding embodiments, wherein said saccharide is in an amount ranging from about 0 to 85% w/w, preferably from about 3% w/w to 80% w/w, 7% to 75%, 10% to 70%, 10% to 50%, 10% to 40%, or from about 10% w/w to 35% w/w.

Embodiment 33

A kit in accordance with any one of the preceding embodiments, wherein said polyol is in a weight ratio relative to said saccharide ranging from about 100:1 to 1:50, preferably from about 50:1 to 1:10; 20:1 to 1:5; 10:1 to 1:2; 6:1 to 1:2; 4:1 to 1:1; or from about 4:1 to 3:2.

Embodiment 34

A kit in accordance with any one of the preceding embodiments, wherein the first unit form further comprises a tonicity modifier.

Embodiment 35

A kit in accordance with any one of the preceding embodiments, wherein the surfactant is selected from the group consisting of polysorbates, such as polysorbate 20 or 80; polyoxyethylene alkyl ethers, such as Brij 35®; or poloxamers, such as Poloxamer 188 or 407; and other ethylene/polypropylene block polymers or polyethyleneglycol (PEG) such as PEG8000.

Embodiment 36

The kit in accordance with any one of the preceding embodiments, wherein the saccharide is sucrose.

Embodiment 37

The kit in accordance with any one of the preceding embodiments, wherein the polyol is mannitol.

Embodiment 38

The kit in accordance with any one of the preceding embodiments, wherein Factor VII polypeptide is present in a concentration of from about 0.6 mg/ml to about 10.0 mg/ml, such as from about 0.6 mg/ml to about 6 mg/ml, from about 0.6 mg/ml to about 5 mg/ml, or from about 0.6 mg/ml to about 4 mg/ml.

Embodiment 39

The kit in accordance with any one of the preceding embodiments, wherein said moisture content is not more than about 2.5% w/w, preferably not more than about 2% w/w, most preferably not more than about 1.5% w/w Embodiment 40

The kit in accordance with any one of the preceding embodiments, wherein the first unit form is a lyophilised cake.

Embodiment 41

The kit in accordance with any one of the preceding embodiments, wherein the first unit form comprises: Factor VII polypeptide, Mannitol, Sucrose, and a surfactant selected from a polysorbate or a poloxamer, such as Tween 80® or Poloxamer 188®.

Embodiment 42

The kit in accordance with embodiment 41, which further contains methionine.

Embodiment 43

A kit in accordance with any one of the preceding embodiments 41 or 42, wherein the second unit form contains L-histidine in an amount of from about 0.1 mM to about 50 mM; such as from about 0.1 mM to about 40 mM; from about 0.1 mM to about 35 mM; from about 0.1 mM to about 30 mM; from about 0.5 mM to about 25 mM; from about 1 mM to about 20 mM; from about 1 mM to about 15 mM; from about 5 mM to about 20 mM; or from about 5 mM to about 15 mM.

Embodiment 44

A kit in accordance with any one of the preceding embodiments 41 to 43, wherein the second unit form further contains one or more components selected from the list of: CaCl2, NaCl, and Glycylglycine.

Embodiment 45

A method for preparing a liquid formulation of a polypeptide, the method comprising the steps of:
a) providing a first and a second unit form as described in any one of embodiments 1 to 44;
b) mixing said first and second unit forms so as to provide a dissolved liquid solution of the composition in the administration vehicle.

Embodiment 46

A method for treating a coagulation factor-responsive syndrome, comprising administering to a subject in need thereof an effective amount of a liquid formulation of a coagulation factor prepared by the method of embodiment 45.

Embodiment 47

A method in accordance with embodiment 46, wherein the coagulation factor-responsive syndrome is haemophilia, and the coagulation factor is Factor VIII or Factor IX; or the syndrome is sepsis, and the coagulation factor is protein C or activated protein C.

Embodiment 48

A method in accordance with embodiment 46 for treating a FVII-responsive syndrome, comprising administering to a subject in need thereof an effective amount of a liquid formulation of said biological agent prepared by the method of embodiment 45.

Embodiment 49

The method in accordance with embodiment 48, wherein said syndrome is selected from the group consisting of haemophilia A, haemophilia B, Factor XI deficiency, Factor VII deficiency, thrombocytopenia, von Willebrand's disease, presence of a clotting factor inhibitor, surgery, trauma, dilutional coagulopathy, and anticoagulant therapy.

Embodiment 50

Use of a Factor VII polypeptide for the preparation of a medicament in the form of a kit as defined in any one of embodiments 1 to 44 for treatment of a Factor VII-responsive syndrome.

Embodiment 51

A composition comprising a Factor VII polypeptide, and at least one stabilizing agent selected from the group consisting of
a) a combination of an antioxidant and mannitol;
b) a combination of methionine and a polyol;
c) a combination of a saccharide and mannitol;
d) a combination of sucrose and a polyol;
e) methionine; and
a polysorbate surfactant in an amount of from about 0.06 to 0.08 mg/mL;
said composition having a moisture content of not more than about 3%;

Embodiment 52

The composition in accordance with embodiment 51, wherein the combination of an antioxidant and mannitol further comprises a saccharide.

Embodiment 53

The composition in accordance with embodiment 51, wherein the combination of methionine and a polyol further comprises a saccharide.

Embodiment 54

The composition in accordance with embodiment 51, wherein the combination of a saccharide and mannitol further comprises an antioxidant.

Embodiment 55

The composition in accordance with embodiment 51, wherein the combination of sucrose and a polyol further comprises an antioxidant.

Embodiment 56

The composition in accordance with any one of the preceding embodiments 51 to 55, wherein the antioxidant is selected from the group consisting of homocysteine, cysteine, cystathionine, methionine, gluthatione, and peptides containing any one of homocysteine, cysteine, cystathionine, methionine and gluthatione.

Embodiment 57

The composition in accordance with any one of the preceding embodiments 51 to 56, wherein the saccharide is selected from the group consisting of sucrose, dextrose, lactose, maltose, trehalose, cyclodextrins, maltodextrins and dextrans.

Embodiment 58

The composition in accordance with any one of the preceding embodiments 51 to 57, wherein the polyol is selected from the group consisting of mannitol, sorbitol and xylitol.

Embodiment 59

The composition in accordance with any one of the preceding embodiments 51 to 58, wherein the composition is stable such that not more than about 5% w/w of the initial content of Factor VII polypeptide is converted to aggregates upon storage of said composition at 30° C. for 8 months, preferably not more than about 4.0% w/w, 3.0% w/w, 2.5% w/w, 2.0% w/w, 1.5% w/w, or not more than about 1.0% w/w, Embodiment 60

The composition in accordance with any one of the preceding embodiments 51 to 59, wherein the composition is stable such that not more than about 6% w/w of the initial content of Factor VII polypeptide is converted to oxidised forms upon storage of said composition at 30° C. for 8 months, preferably not more than about 5% w/w, 4.0% w/w, 3.0% w/w, 2.5% w/w, 2.0% w/w, or not more than about 1.5% w/w.

Embodiment 61

The composition in accordance with any one of the preceding embodiments 51 to 60, wherein said polyol is in an amount ranging from about 5% w/w to 90% w/w, preferably from about 18% w/w to 88% w/w, 18% to 83%, 25% to 80%, 40% to 80%, 50% to 80%, or from about 50% w/w to 70% w/w.

Embodiment 62

The composition in accordance with any one of the preceding embodiments 51 to 61, wherein said saccharide is in an amount ranging from about 0 to 85% w/w, preferably from about 3% w/w to 80% w/w, 7% to 75%, 10% to 70%, 10% to 50%, 10% to 40%, or from about 10% w/w to 35% w/w.

Embodiment 63

The composition in accordance with any one of the preceding embodiments 51 to 62, wherein said polyol is in a weight ratio relative to said saccharide ranging from about 100:1 to 1:50, preferably from about 50:1 to 1:10; 20:1 to 1:5; 10:1 to 1:2; 6:1 to 1:2; 4:1 to 1:1; or from about 4:1 to 3:2.

Embodiment 64

The composition in accordance with any one of the preceding embodiments 51 to 63, further comprising an agent suitable for keeping the pH of said composition in the range of 3 to 9 when dissolved in aqueous solvent, preferably the pH is in the range of 4 to 7, more preferred in the range of 4.5 to 6.5, even more preferred in the range of 5.5 to 6.5.

Embodiment 65

The composition in accordance with embodiment 64, wherein said agent is selected from the group consisting of: citric acid, acetic acid, histidine, malic acid, phosphoric acid, tartaric acid, succinic acid, MES, HEPES, imidazole, TRIS, imidazol, lactic acid, glutaric acid, PIPES and glycylglycine, or a mixture of at least two such listed agents, wherein the mixture is able to provide a pH value in the specified range.

Embodiment 66

The composition in accordance with any one of the preceding embodiments 51 to 65, further comprising a tonicity modifier.

Embodiment 67

The composition in accordance with embodiment 66, wherein the tonicity modifier is selected from the group consisting of: sodium acetate, sodium lactate, sodium chloride, potassium chloride, calcium chloride, mannitol, glycerol, and propylene glycol.

Embodiment 68

The composition in accordance with any one of the preceding embodiments 51 to 67, wherein the surfactant is selected from the group consisting of polysorbate 20 or 80, preferably polysorbate 80.

Embodiment 69

The composition in accordance with any one of the preceding embodiments 51 to 68, wherein the saccharide is sucrose.

Embodiment 70

The composition in accordance with any one of the preceding embodiments 51 to 69, wherein the polyol is mannitol.

Embodiment 71

The composition in accordance with any one of the preceding embodiments 51 to 70, wherein the Factor VII Polypeptide is selected from the group consisting of Human Factor VIIa, Recombinant Human Factor VIIa and a Factor VII Sequence Variant.

Embodiment 72

The composition in accordance with embodiment 71, wherein the Factor VII Polypeptide is Human Factor VIIa or Recombinant Human Factor VIIa.

Embodiment 73

The composition in accordance with any one of the preceding embodiments 51 to 72, wherein the Factor VII Polypeptide is a Factor VII-related polypeptide wherein the ratio between the activity of said Factor VII-related polypeptide and wild-type Factor VII is at least 1.25 when tested in one or more of the "In Vitro Proteolysis Assay" and the "in Vitro Hydrolysis Assay" as described in the present specification.

Embodiment 74

The composition in accordance with any one of the preceding embodiments 51 to 73, wherein Factor VII polypeptide is present in a concentration of from about 0.6 mg/ml to about 10.0 mg/ml, such as from about 0.6 mg/ml to about 6 mg/ml, from about 0.6 mg/ml to about 5 mg/ml, or from about 0.6 mg/ml to about 4 mg/ml.

Embodiment 75

The composition in accordance with any one of the preceding embodiments 51 to 74, wherein said moisture content is not more than about 2.5% w/w, preferably not more than about 2% w/w, most preferably not more than about 1.5% w/w Embodiment 76

The composition in accordance with any one of the preceding embodiments 51 to 75, wherein the composition is a lyophilised cake.

Embodiment 77

The composition in accordance with any one of the preceding embodiments, wherein the composition comprises: Factor VII polypeptide, Mannitol, Sucrose, and poloxamer 80, such as Tween 80®.

Embodiment 78

The composition in accordance with embodiment 77, which further contains methionine.

Embodiment 79

The composition in accordance with any one of the preceding embodiments 77 to 78, which further contains L-histidine.

Embodiment 80

The composition in accordance with any one of the preceding embodiments 77 to 79, which further contains one or more components selected from the list of: CaCl2, NaCl, and Glycylglycine.

Embodiments 81

Compositions in accordance with any one of the preceding embodiments 51 to 80, selected from the list of:

| Compound | Formulation I-81 | Formulation II-81 |
| --- | --- | --- |
| FVII polypeptide | 0.6 to 10 mg/ml | 0.6 to 10 mg/ml |
| Mannitol | 20 to 40 mg/ml | 20 to 40 mg/ml |
| Sucrose | 5 to 20 mg/ml | — |
| Methionine | 0-1 mg/ml | 0-1 mg/ml |
| Tween 80 | 0.06 to 0.08 mg/ml | 0.06 to 0.08 mg/ml |
| pH | 5.0 to 7.0 | 5.0 to 7.0 |

Embodiment 82

Compositions in accordance with embodiment 81, selected from the list of:

| Compound | Formulation III-82 | Formulation IV-82 |
| --- | --- | --- |
| FVIIa polypeptide | 0.6 to 3.0 mg/ml | 0.6 to 3.0 mg/mL |
| Mannitol | 25 mg/ml | 25 mg/ml |
| Sucrose | 10 mg/ml | 10 mg/ml |
| Methionine | 0.5 mg/ml | — |
| Tween 80 | 0.06 to 0.08 mg/ml | 0.06 to 0.08 mg/ml |
| pH | 5.5 to 6.5 | 5.5 to 6.5 |

Embodiment 83

Compositions in accordance with any one of the preceding embodiments 81 or 82, containing polysorbate 80 in an amount of about 0.07 mg/mL.

Embodiment 84

Compositions in accordance with any one of the preceding embodiments 81 to 83, containing FVIIa polypeptide in an amount of about 1.0 mg/mL Embodiment 85

Compositions in accordance with any one of the preceding embodiments 81 to 84, further comprising at least one of the components selected from the list of: Ca2+ in an amount of about 10 mM, preferably as CaCl2×2H2O; NaCl in an amount of about 50 mM or about 40 mM, e.g., 39 mM; Histidine, preferably L-Histidine in an amount of about 10 mM.

Embodiment 86

Compositions in accordance with any one of the preceding embodiments 81 to 85, having a pH of 5.5, or 5.6, or 5.7, or, 5.8, or 5.9, or 6.0, or 6.1, or 6.2, or 6.3, or 6.4, or 6.5.

Embodiment 87

A method of preparing the compositions defined in embodiments 51 to 86, comprising the steps of:
i) providing a Factor VII polypeptide in a solution comprising at least one stabilizing agent selected from the group consisting of
a) a combination of an antioxidant and mannitol;
b) a combination of methionine and a polyol;
c) a combination of a saccharide and mannitol;
d) a combination of sucrose and a polyol; and
e) methionine; and
a polysorbate surfactant in an amount of from about 0.06 to 0.08 mg/mL;
ii) processing said solution so as to obtain a solid composition with a moisture content not more than about 3% w/w.

Embodiment 88

A method in accordance with embodiment 87, wherein the antioxidant is selected from the group consisting of homocysteine, cysteine, cystathionine, methionine, gluthatione, and peptides containing any one of homocysteine, cysteine, cystathionine, methionine and gluthatione.

Embodiment 89

A method in accordance with embodiment 87, wherein the saccharide is selected from the group consisting of sucrose, dextrose, lactose, maltose, trehalose, cyclodextrins, maltodextrins and dextrans.

Embodiment 90

A method in accordance with embodiment 87, wherein the polyol is selected from the group consisting of mannitol, sorbitol and xylitol.

Embodiment 91

A method in accordance with embodiment 87, wherein the polyol is present in an amount ranging from about 0.5 to about 75 mg/ml, preferably from about 2 to 45 mg/ml, such as from about 5 mg/ml to 45 mg/ml, from about 5 to 35 mg/ml, from about 5 to 25 mg/ml, 5 to 20 mg/ml, 20 to 40 mg/ml, or from about 20 to about 30 mg/ml, Embodiment 92

A method in accordance with embodiment 87, wherein the saccharide is present in an amount ranging from about 0.5 to 75 mg/ml, preferably from about 2 to 45 mg/ml, such as from about 5 mg/ml to 45 mg/ml, from about 5 to 35 mg/ml, from about 5 to 25 mg/ml, or from about 5 to 20 mg/ml.

Embodiment 93

A method in accordance with embodiment 87, wherein the antioxidant is in an amount ranging from about 0.05 to 10 mg/ml, preferably from about 0.1 to 5 mg/ml, more preferably from about 0.1 mg/ml to 2.5 mg/ml, even more preferably from about 0.1 to 2 mg/ml, most preferably from about 0.1 to 1 mg/ml.

Embodiment 94

A method in accordance with embodiment 87, wherein the saccharide is sucrose.

Embodiment 95

A method in accordance with embodiment 87, wherein the antioxidant is methionine.

Embodiment 96

A method in accordance with embodiment 87, wherein the polyol is mannitol.

Embodiment 97

A method in accordance with embodiment 87, wherein the processing comprises freeze-drying.

Embodiment 98

A method for treating a FVII-responsive syndrome, comprising administering to a subject in need thereof an effective amount of a composition as defined in any one of embodiments 51 to 86.

Embodiment 99

The method in accordance with embodiment 98, wherein said syndrome is selected from the group consisting of haemophilia A, haemophilia B, Factor XI deficiency, Factor VII deficiency, thrombocytopenia, von Willebrand's disease, presence of a clotting factor inhibitor, surgery, trauma, dilutional coagulopathy, and anticoagulant therapy.

Embodiment 100

Use of Factor VII polypeptide for the preparation of a medicament for treating a Factor VII-responsive syndrome, said medicament comprising a composition as defined in any one of embodiments 51 to 86.

Embodiment 101

The use in accordance with embodiment 100, wherein said syndrome is selected from the group consisting of haemophilia A, haemophilia B, Factor XI deficiency, Factor VII deficiency, thrombocytopenia, von Willebrand's disease, presence of a clotting factor inhibitor, surgery, trauma, and anticoagulant therapy.

The following examples are offered by way of illustration, not by way of limitation:

EXAMPLES

General methods

Example 1

Analytical Methods Used in Determining Stability Indicating Parameters

A. Determination of Oxidised Forms by Reverse Phase HPLC (RP-HPLC):

HPLC Column: 4.5×250 mm column packed with butyl-bonded silica with a particle size of 5 μm and pore size 300 Å. Column temperature: 70° C. Eluent A: water 99.9% v/v and trifluoracetic acid 0.1% v/v. Eluent B: acetonitrile 80% v/v. trifluoracetic acid 0.09% v/v and water 19.91% v/v. The column was eluted with a linear gradient from X % B to (X+13) % B in 30 minutes. Flow rate: 1.0 ml/min. Detection: 214 nm.

The oxidised forms are methionine sulfoxides of Factor VII Polypeptides. For example the two main derivatives of FVII are Met(O)298 FVII and Met(O)306 FVII.

The content of oxidised forms is expressed as the percentage of the initial amount of Factor VII in the composition upon preparation that is recovered as oxidised forms of Factor VII.

B. Determination of Aggregates of Factor VII Polypeptides by High Performance Gel Permeation Chromatography (GP-HPLC).

GP-HPLC was run on a Waters Polypeptide Pak 300 SW column. 7.5×300 mm. using 0.2 M ammoniumsulfat pH 7.0 containing 5% isopropanol as the mobile phase. Flow rate: 0.5 ml/min and detection: 215 nm.

The content of aggregates is expressed as the percentage of the initial amount of Factor VII in the composition upon preparation that is recovered as dimeric, oligomeric and polymeric forms of Factor VII.

Example 2

Assays for Testing Biological Activity of Factor VII Polypeptides

Test for Factor VIIa Activity:

A suitable assay for testing for Factor VIIa activity and thereby selecting suitable Factor VIIa variants can be performed as a simple preliminary in vitro test: (the "In Vitro Hydrolysis Assay").

In Vitro Hydrolysis Assay

Native (wild-type) Factor VIIa and Factor VIIa variant (both hereafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

$$\text{Ratio}=(A_{405\ nm}\ \text{Factor } VIIa \text{ variant})/(A_{405\ nm}\ \text{Factor } VIIa \text{ wild-type}).$$

Based thereon, Factor VIIa variants with an activity comparable to or higher than native Factor VIIa may be identified, such as, for example, variants where the ratio between the activity of the variant and the activity of native Factor VII (wild-type FVII) is around, versus above 1.0.

The activity of Factor VIIa or Factor VIIa variants may also be measured using a physiological substrate such as Factor X, suitably at a concentration of 100-1000 nM, where the Factor Xa generated is measured after the addition of a suitable chromogenic substrate (eg. S-2765) ("the In Vitro Proteolysis Assay"). In addition, the activity assay may be run at physiological temperature.

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl2 and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A$405 nm Factor *VIIa* variant)/($A$405 nm Factor *VIIa* wild-type).

Based thereon, Factor VIIa variants with an activity comparable to or higher than native Factor VIIa may be identified, such as, for example, variants where the ratio between the activity of the variant and the activity of native Factor VII (wild-type FVII) is around, versus above 1.0.

Thrombin Generation Assay:

The ability of Factor VII or Factor VII-related polypeptides or Factor VIII or Factor VIII-related polypeptides (e.g., variants) to generate thrombin can be measured in an assay comprising all relevant coagulation Factors and inhibitors at physiological concentrations and activated platelets (as described on p. 543 in Monroe et al. (1997) Brit. J. Haematol. 99, 542-547 which is hereby incorporated as reference).

Clot Assay:

The activity of the Factor VII polypeptides may also be measured using a one-stage clot assay (assay 4) essentially as described in WO 92/15686 or U.S. Pat. No. 5,997,864. Briefly, the sample to be tested is diluted in 50 mM Tris (pH 7.5), 0.1% BSA and 100 µL is incubated with 100 µL of Factor VII deficient plasma and 200 µL of thromboplastin C containing 10 mM $Ca^{2+}$. Clotting times are measured and compared to a standard curve using a reference standard or a pool of citrated normal human plasma in serial dilution.

Working Examples

Example 3

Stability Data for Compositions of rFVIIa Freeze Dried with and without Histidine, Respectively It will be seen that it is an advantage to freeze-dry without the presence of Histidine as less Dimers/Oligomers will be formed.

Compositions

| Composition | A1 | B1 | C1 | D1 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | 1.32 mg/mL | 1.32 mg/mL |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 6.0 | 6.0 |

| Composition | E1 | F1 | G1 | H1 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | 1.32 mg/mL | 1.32 mg/mL |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 6.0 | 6.0 |

| Composition | I1 | J1 | K1 | L1 |
|---|---|---|---|---|
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | 1.32 mg/mL | 1.32 mg/mL |
| L-Histidine | — | 1.55 mg/mL | — | 1.55 mg/mL |
| Polysorbate 80 | 0.1 mg/mL | 0.1 mg/mL | 0.1 mg/mL | 0.1 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 6.0 | 6.0 |

For reconstitution of compositions A1, C1, E1, G1, I1, and K1 Histidine solvens 1.55 mg/mL will be used; for composition B1, D1, F1, H1, J1, and L1 will be used Water for injection (WFI).

Example 4

Stability Data for Compositions of rFVIIa Freeze Dried with and without Histidine, and/or Glycylglycine, and/or NaCl, Respectively It will be seen that it is an advantage to freeze-dry without the presence of NaCl as this will decrease the risk of collapse of the cake.

| Composition | A2 | B2 | C2 | D2 |
|---|---|---|---|---|
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

-continued

| Composition | | | | |
|---|---|---|---|---|
| | E2 | F2 | G2 | H2 |
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.50 | 5.50 | 5.50 | 5.50 |

| Composition | | | | |
|---|---|---|---|---|
| | I2 | J2 | K2 | L2 |
| rFVIIa | 1.0 mg/mL | 1.0 mg/mL | 1.0 mg/mL | 1.0 mg/mL |
| Sodium chloride | 2.92 mg/mL | 2.92 mg/mL | 2.92 mg/mL | 2.92 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | | | | |
|---|---|---|---|---|
| | M2 | N2 | O2 | P2 |
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | | | | |
|---|---|---|---|---|
| | Q2 | R2 | S2 | T2 |
| rFVIIa | 1.0 mg/mL | 1.0 mg/mL | 1.0 mg/mL | 1.0 mg/mL |
| Sodium chloride | 2.34 mg/mL | 2.34 mg/mL | 2.34 mg/mL | 2.34 mg/mL |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

| Composition | | | | |
|---|---|---|---|---|
| | U2 | V2 | X2 | Y2 |
| rFVIIa | 1.0 mg/mL | 1.0 mg/mL | 1.0 mg/mL | 1.0 mg/mL |
| Sodium chloride | — | — | — | — |
| Calcium chloride 2H2O | 1.47 mg/mL | 1.47 mg/mL | 1.47 mg/mL | 1.47 mg/mL |
| Glycylglycine | 1.32 mg/mL | 1.32 mg/mL | — | — |
| L-Histidine | — | 1.55 mg/mL | — | 1.55 mg/mL |
| Polysorbate 80 | 0.07 mg/mL | 0.07 mg/mL | 0.07 mg/mL | 0.07 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 6.0 | 6.0 | 6.0 | 6.0 |

For reconstitution, Histidine solvens 1.55 mg/mL will be used for Composition A2, I2, and Q2; for composition B2, J2, and R2 will be used Water for injection (WFI).

For reconstitution, Histidine solvens 1.55 mg/mL will be used for Composition C2, K2, and S2; for composition D2, L2, and T2 will be used Water for injection (WFI).

For reconstitution, Histidine solvens 1.55 mg/mL with NaCl 2.92 mg/mL will be used for Composition E2, M2, and U2; for composition F2, N2, and V2 will be used Saline Water 2.92 mg/mL.

For reconstitution, Histidine solvens 1.55 mg/mL with NaCl 2.92 mg/mL will be used for Composition G2, O2, and X2; for composition H2, P2, and Y2 will be used Saline Water 2.92 mg/mL.

Example 5

Manufacturing of Compositions

In general, the compositions were prepared from a purified bulk solution. Excipients were added, and the solution was diluted to the desired concentration of rFVIIa. The resulting solution was sterile filtered using a sterilised membrane filter (0.2 micron pore size or equivalent) and filled into sterile glass vials. The vials were freeze-dried, closed with rubber stoppers, and sealed with aluminium flip-off type caps.

Example 6

Comparison of Content of Soluble Aggregates Formed in Formulations with and without Addition of L-Histidine before Freeze-Drying The following formulations were prepared (all concentrations stated in mg/ml):

| | Formulation no. | | | |
|---|---|---|---|---|
| Ingredient | 1 | 2 | 3 | 4 |
| rFVIIa | 1.0 | 1.0 | 1.0 | 1.0 |
| NaCl | 2.34 | 2.34 | 2.34 | 2.34 |
| CaCl2, 2H2O | 1.47 | 1.47 | 1.47 | 1.47 |
| Glycylglycine | 1.32 | 1.32 | 1.32 | 1.32 |
| Polysorbate 80 | 0.1 | 0.1 | 0.1 | 0.1 |
| L-Methionine | 0.5 | 0.5 | 0.5 | 0.5 |
| L-Histidine | — | — | 1.55 | 1.55 |
| Mannitol | 30 | 25 | 30 | 25 |
| Sucrose | 8 | 12 | 8 | 12 |
| pH | 6.0 | 6.0 | 6.0 | 6.0 |

The formulations were prepared as described in example 5 using a filling volume of 5.3 ml. After freeze-drying the contents of dimer, oligomer, and polymer forms were measured by GP-HPLC as described in example 3. The results are stated below:

| | Formulation no. | | | |
|---|---|---|---|---|
| | 1 | 2 | 3 | 4 |
| Dimer and oligomer forms (%) | 1.8 | 1.6 | 2.5 | 2.7 |
| Polymer forms (%) | <0.3 | <0.3 | <0.3 | <0.3 |

The results show that formulations 1 and 2 without addition of L-histidine had lower contents of dimer and oligomer forms after freeze-drying as compared to the corresponding formulations 3 and 4, which contained L-histidine.

Example 7

Stability of a Freeze-Dried rFVIIa Formulation

A formulation containing

| | |
|---|---|
| rFVIIa | 1.0 mg/ml |
| NaCl | 2.34 mg/ml |
| CaCl2, 2H2O | 1.47 mg/ml |
| Glycylglycine | 1.32 mg/ml |
| Polysorbate 80 | 0.07 mg/ml |
| L-Methionine | 0.5 mg/ml |
| Mannitol | 25 mg/ml |
| Sucrose | 10 mg/ml |
| pH 6.0 | | was prepared by as described in example 5 using filling volumes of 1.1 ml.

The formulation was placed at 25° C. and 40° C. in darkness. Samples were collected according to the tables below. After reconstitution of the freeze-dried product in 10 mM L-histidine solvent, the contents of dimer/oligomer/polymer and oxidised forms were measured as described in example 3, while the activity was determined by one-stage clot assay as described in example 4.

| | Storage time at 25° C. (months) | | |
|---|---|---|---|
| Parameter | 0 | 3 | 6 |
| Dimer/oligomer forms (%) | 1.6 | 2.0 | 2.1 |
| Polymer forms (%) | <0.3 | <0.3 | <0.3 |
| Oxidised forms (%) | 1.4 | 1.3 | 1.4 |
| Activity (IU/ml) | 58000 | 54400 | n.d. |

| | Storage time at 40° C. (months) | | | |
|---|---|---|---|---|
| Parameter | 0 | 1 | 3 | 6 |
| Dimer/oligomer forms (%) | 1.6 | 2.4 | 2.5 | 2.4 |
| Polymer forms (%) | <0.3 | 0.4 | 0.4 | <0.3 |
| Oxidised forms (%) | 1.4 | 1.2 | 1.3 | 1.5 |
| Activity (IU/ml) | 58000 | 53600 | 53300 | n.d. | n.d.: not determined

Example 8

The influence of sodium chloride on the visual appearance of the freeze dried cake was investigated in a factorial design study. Among the variable parameters was the content of sodium chloride. The result of four formulations included in the study is shown in the table

| Formulation no. | Content of Sodium chloride (mg/mL) | Visual appearance |
|---|---|---|
| 1 | 0 | Solid homogeneous cake |
| 2 | 0 | Solid homogeneous cake |
| 3 | 3.50 | Partly collapsed cake |
| 4 | 3.50 | Partly collapsed cake |

All formulations further contained:

| | |
|---|---|
| rFVIIa | 1.0 mg/mL |
| Calcium chloride | 1.47 mg/mL |
| Glycylglycine | 1.32 mg/mL |
| Polysorbate 80 | 0.1 mg/mL |
| Mannitol | 40 mg/mL |
| Sucrose | 10 mg/mL |

In addition formulations 1 and 2 contained 0.5 mg/mL methionine.

pH was adjusted to:
6.0 (formulations 1 and 4)
5.0 (formulations 2 and 3)

Example 9

Stability Data for Compositions of FVII Polypeptide

It will be seen that the compositions are stable with regard to formation of dimers/oligomers after storage at 25° C. for 6 months.

| Compositions | | | | |
|---|---|---|---|---|
| | Composition | | | |
| | A-9 | B-9 | C-9 | D-9 |
| V158D/E296V/M298Q-FVII | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

| | Composition | | | |
|---|---|---|---|---|
| | E-9 | F-9 | G-9 | H-9 |
| V158D/E296V/M298Q-FVII | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H20 | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

For reconstitution of compositions A-9 to H-9 Water for injection (WFI) will be used.

For reconstitution of compositions B-9, D-9, F-9, and H-9 Histidine solvens 1.55 mg/mL may also be used.

Compositions containing the same ingredients and amounts of ingredients as compositions A-9 to H-9 but having a pH of 4.5 were also prepared. Furthermore, compositions containing the same ingredients and amounts of ingredients as compositions A-9 to H-9 but having a pH of 5.5 were also prepared.

For reconstitution of compositions A-9-1 to H-9-1 Water for injection (WFI) will be used.

For reconstitution of compositions B-9-1, D-9-1, F-9-1, and H-9-1 Histidine solvens 1.55 mg/mL may also be used.

Compositions containing the same ingredients and amounts of ingredients as compositions A-9-1 to H-9-1 but having a pH of 4.5 were also prepared. Furthermore, compositions containing the same ingredients and amounts of ingredients as compositions A-9-1 to H-9-1 but having a pH of 5.5 were also prepared.

| | Composition | | | |
|---|---|---|---|---|
| | A-9-1 | B-9-1 | C-9-1 | D-9-1 |
| V158D/M298Q-FVII | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H20 | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

| | Composition | | | |
|---|---|---|---|---|
| | E-9-1 | F-9-1 | G-9-1 | H-9-1 |
| V158D/M298Q-FVII | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H20 | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

|  | Composition | | | |
| --- | --- | --- | --- | --- |
|  | A-9-2 | B-9-2 | C-9-2 | D-9-2 |
| K337A-FVII | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

|  | Composition | | | |
| --- | --- | --- | --- | --- |
|  | E-9-2 | F-9-2 | G-9-2 | H-9-2 |
| K337A-FVII | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

For reconstitution of compositions A-9-2 to H-9-2 Water for injection (WFI) will be used.

For reconstitution of compositions B-9-2, D-9-2, F-9-2, and H-9-2 Histidine solvens 1.55 mg/mL may also be used.

Compositions containing the same ingredients and amounts of ingredients as compositions A-9-2 to H-9-2 but having a pH of 4.5 were also prepared. Furthermore, compositions containing the same ingredients and amounts of ingredients as compositions A-9-2 to H-9-2 but having a pH of 5.5 were also prepared.

|  | Composition | | | |
| --- | --- | --- | --- | --- |
|  | A-9-3 | B-9-3 | C-9-3 | D-9-3 |
| M298Q-FVIIa | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

|  | Composition | | | |
| --- | --- | --- | --- | --- |
|  | E-9-3 | F-9-3 | G-9-3 | H-9-3 |
| M298Q-FVIIa | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

For reconstitution of compositions A-9-3 to H-9-3 Water for injection (WFI) will be used.

For reconstitution of compositions B-9-3, D-9-3, F-9-3, and H-9-3 Histidine solvens 1.55 mg/mL may also be used.

Compositions containing the same ingredients and amounts of ingredients as compositions A-9-3 to H-9-3 but having a pH of 4.5 were also prepared. Furthermore, compositions containing the same ingredients and amounts of ingredients as compositions A-9-3 to H-9-3 but having a pH of 5.5 were also prepared.

For reconstitution of compositions B-9-4, D-9-4, F-9-4, and H-9-4 Histidine solvens 1.55 mg/mL may also be used.

Compositions containing the same ingredients and amounts of ingredients as compositions A-9-4 to H-9-4 but having a pH of 4.5 were also prepared. Furthermore, compositions containing the same ingredients and amounts of ingredients as compositions A-9-4 to H-9-4 but having a pH of 5.5 were also prepared.

| | Composition | | | |
|---|---|---|---|---|
| | A-9-4 | B-9-4 | C-9-4 | D-9-4 |
| V158D/E296V/M298Q/K337A-FVIIa | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

| | Composition | | | |
|---|---|---|---|---|
| | E-9-4 | F-9-4 | G-9-4 | H-9-4 |
| V158D/E296V/M298Q/K337A-FVIIa | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

For reconstitution of compositions A-9-4 to H-9-4 Water for injection (WFI) will be used.

| | Composition | | | |
|---|---|---|---|---|
| | A-9-5 | B-9-5 | C-9-5 | D-9-5 |
| V158D/E296V/M298Q/L305V-FVIIa | 0.6 mg/mL | 0.6 mg/mL | 0.6 mg/mL | 0.6 mg/mL |
| Sodium chloride | 40 mM (2.34 mg/mL) | 40 mM (2.34 mg/mL) | 40 mM (2.34 mg/mL) | 40 mM (2.34 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

| | Composition | | | |
|---|---|---|---|---|
| | E-9-5 | F-9-5 | G-9-5 | H-9-5 |
| V158D/E296V/M298Q/L305V-FVIIa | 0.6 mg/mL | 0.6 mg/mL | 0.6 mg/mL | 0.6 mg/mL |
| Sodium chloride | — | 50 mM (2.92 mg/mL) | — | 50 mM (2.92 mg/mL) |
| Calcium chloride 2H2O | 10 mM (1.47 mg/mL) | 10 mM (1.47 mg/mL) | 10 mM (1.47 mg/mL) | 10 mM (1.47 mg/mL) |
| Glycylglycine | — | — | — | — |
| L-Histidine | 10 mM (1.55 mg/mL) | — | 10 mM (1.55 mg/mL) | — |

| | | | | |
|---|---|---|---|---|
| Polysorbate 80 | 0.07 mg/mL | 0.07 mg/mL | 1.0 mg/mL | 1.0 mg/mL |
| Methionine | 0.5 mg/mL | 0.5 mg/mL | 0.5 mg/mL | 0.5 mg/mL |
| Mannitol | 25 mg/mL | 25 mg/mL | 25 mg/mL | 25 mg/mL |
| Sucrose | 10 mg/mL | 10 mg/mL | 10 mg/mL | 10 mg/mL |
| pH | 5.0 | 5.0 | 5.0 | 5.0 |

For reconstitution of compositions A-9-5 to H-9-5 Water for injection (WFI) will be used.

For reconstitution of compositions B-9-5, D-9-5, F-9-5, and H-9-5 Histidine solvens 1.55 mg/mL may also be used.

Compositions containing the same ingredients and amounts of ingredients as compositions A-9-5 to H-9-5 but having a pH of 4.5 were also prepared. Furthermore, compositions containing the same ingredients and amounts of ingredients as compositions A-9-5 to H-9-5 but having a pH of 5.5 were also prepared.

The invention claimed is:

1. A kit comprising a first unit form and a second unit form, wherein
   a) the first unit form comprising a composition comprising
      (i) a blood coagulation factor polypeptide and
      (ii) at least one stabilizing agent selected from the group consisting of: surfactants, antioxidants, saccharides, polyols, and combinations of any of the foregoing, wherein the composition has a moisture content of not more than about 3%, in the first unit form, and
      (iii) a container for containing the first unit form; and,
   b) the second unit form comprising an administration vehicle comprising
      (i) a solvent for reconstitution of the composition;
      (ii) an agent suitable for keeping the pH of the composition in the range of 3 to 9 when dissolved in aqueous solvent, wherein the agent comprises histidine, and wherein the histidine is present in an amount of from about 0.1 mM to 100 mM; and
      (iii) a container for containing the second unit form.

2. The kit according to claim 1, wherein the administration vehicle further comprises (iv) at least one component selected from the group of: surfactants, antioxidants, saccharides, and polyols.

3. The kit according to claim 1, wherein the polypeptide is selected from the group consisting of: human Factor VIII, human Factor VIIa, human Factor IX, human Factor X, activated human Protein C, and a Factor VII sequence variant.

4. The kit according to claim 3, wherein Factor VII polypeptide is present in a concentration of from about 0.6 mg/ml to about 10.0 mg/ml.

5. The kit according to claim 1, wherein the agent suitable for keeping the pH of said composition in the range of 3 to 9 when dissolved in aqueous solvent is present at a concentration from about 0.1 mM to about 50 mM.

6. The kit according to claim 1, wherein the agent suitable for keeping the pH of said composition in the range of 3 to 9 when dissolved in aqueous solvent further comprises one or more of citric acid, acetic acid, malic acid, phosphoric acid, tartaric acid, succinic acid, MES, HEPES, imidazole, TRIS, lactic acid, glutaric acid, PIPES, glycylglycine, and combinations of any of the foregoing, wherein a mixture of the agents suitable for keeping the pH of said composition is able to provide a pH between 3 and 9.

7. The kit according to claim 1, further comprises a tonicity modifying agent in an amount sufficient to make essentially isotonic the reconstituted solution resulting from dissolving the composition of the first unit form in the administration vehicle of the second unit form, wherein the tonicity modifying agent is selected from the group consisting of: sodium acetate, sodium lactate, sodium chloride, potassium chloride, calcium chloride, magnesium chloride, mannitol, glycerol, propylene glycol, and combinations of any of the foregoing.

8. The kit according to claim 1, wherein the first unit form comprises at least one stabilizing agent selected from the group consisting of
   a) a combination of an antioxidant and mannitol;
   b) a combination of methionine and a polyol;
   c) a combination of a saccharide and mannitol;
   d) a combination of sucrose and a polyol;
   e) methionine; and
   f) a surfactant.

9. The kit according to claim 1, wherein the antioxidant is selected from the group consisting of homocysteine, cysteine, cystathionine, methionine, and gluthatione.

10. The kit according to claim 1, wherein the saccharide is selected from the group consisting of sucrose, dextrose, lactose, maltose, trehalose, cyclodextrins, maltodextrins, and dextrans.

11. The kit according to claim 1, wherein the polyol is selected from the group consisting of mannitol, sorbitol, and xylitol.

12. The kit according to claim 1, wherein the first unit form further comprises a tonicity modifier.

13. A method for preparing a liquid formulation of a blood coagulation factor polypeptide, the method comprising the steps of:
    a) providing the first and the second unit form as defined in claim 1;
    b) mixing the composition of said first unit form and the administration vehicle of said second unit form so as to provide a dissolved liquid solution of the composition in the administration vehicle.

14. The kit of claim 1, wherein the kit further comprising a pharmaceutical medicament.

15. The kit of claim 1, wherein the composition comprises
    (i) a Factor VII polypeptide and
    (ii) at least one stabilizing agent, selected from the group consisting of
       a) a combination of an antioxidant and mannitol;
       b) a combination of methionine and a polyol;
       c) a combination of a saccharide and mannitol;
       d) a combination of sucrose and a polyol;
       e) methionine; and
       f) a polysorbate surfactant;
    wherein said composition has a moisture content of not more than about 3%, and wherein the composition is free of histidine.

16. The kit of claim 15, wherein the composition is selected from the group consisting of Formulation i, Formulation ii, Formulation iii, Formulation iv, Formulation v, and Formulation vi, wherein each Formulation comprises the compounds listed herein and wherein each formulation has a pH and concentration as listed herein when reconstituted with the administration vehicle of the second unit form:

| Compound | Formulation i | Formulation ii |
|---|---|---|
| FVII polypeptide | 0.6 to 10 mg/ml | 0.6 to 10 mg/ml |
| Mannitol | 20 to 40 mg/ml | 20 to 40 mg/ml |
| Sucrose | 5 to 20 mg/ml | — |
| Methionine | 0-1 mg/ml | 0-1 mg/ml |
| Polysorbate | 0.06 to 0.08 mg/ml | 0.06 to 0.08 mg/ml |
| pH | 5.0 to 7.0 | 5.0 to 7.0 |

| Compound | Formulation iii | Formulation iv |
|---|---|---|
| FVIIa polypeptide | 0.6 to 3.0 mg/ml | 0.6 to 3.0 mg/ml |
| Mannitol | 25 mg/ml | 25 mg/ml |
| Sucrose | 10 mg/ml | 10 mg/ml |
| Methionine | 0.5 mg/ml | — |
| Polysorbate | 0.06 to 0.08 mg/ml | 0.06 to 0.08 mg/ml |
| pH | 5.5 to 6.5 | 5.5 to 6.5 |

| Compound | Formulation v | Formulation vi |
|---|---|---|
| FVIIa polypeptide | 0.6 to 3.0 mg/ml | 0.6 to 3.0 mg/ml |
| Mannitol | 25 mg/ml | 25 mg/ml |
| Sucrose | 10 mg/ml | 10 mg/ml |
| Methionine | 0.5 mg/ml | — |
| Polysorbate | 0.06 to 0.08 mg/ml | 0.06 to 0.08 mg/ml |
| pH | 5.0 to 6.0 | 5.0 to 6.0. |

17. The kit of claim 16, wherein the administrative vehicle comprises 10 mM histidine.

* * * * *